(12) United States Patent
Hain et al.

(10) Patent No.: US 9,572,315 B2
(45) Date of Patent: Feb. 21, 2017

(54) **ALS INHIBITOR HERBICIDE TOLERANT *B. NAPUS* MUTANTS**

(75) Inventors: Rüdiger Hain, Frankfurt am Main (DE); Günter Donn, Hofheim (DE); Nathalie Knittel-Ottleben, Kriftel (DE); Heinrich Busch, Delbrück (DE); Carsten Oertel, Lippstadt (DE); Dieter Stelling, Langenberg (DE)

(73) Assignees: BAYER INTELLECTUAL PROPERTY GMBH, Monheim (DE); DEUTSCHE SAATVEREDELUNG AG, Lippstadt (DE)

( * ) Notice: Subject to any disclaimer, the term of this patent is extended or adjusted under 35 U.S.C. 154(b) by 0 days.

(21) Appl. No.: 14/115,122

(22) PCT Filed: May 4, 2012

(86) PCT No.: PCT/EP2012/058239
§ 371 (c)(1),
(2), (4) Date: Nov. 20, 2013

(87) PCT Pub. No.: WO2012/150335
PCT Pub. Date: Nov. 8, 2012

(65) Prior Publication Data
US 2014/0066643 A1    Mar. 6, 2014

Related U.S. Application Data

(60) Provisional application No. 61/482,287, filed on May 4, 2011.

(30) Foreign Application Priority Data

May 4, 2011    (EP) .................................... 11164720

(51) Int. Cl.
*A01H 5/10*    (2006.01)
*C12N 15/82*    (2006.01)
*C12N 9/88*    (2006.01)

(52) U.S. Cl.
CPC ................ *A01H 5/10* (2013.01); *C12N 9/88* (2013.01); *C12N 15/8274* (2013.01); *C12N 15/8278* (2013.01); *C12Y 401/03* (2013.01)

(58) Field of Classification Search
CPC .............. A01H 5/10; C12N 5/04; C12Q 1/68
See application file for complete search history.

(56) References Cited

U.S. PATENT DOCUMENTS

| | | |
|---|---|---|
| 7,595,177 B2 | 9/2009 | Barnes et al. |
| 2004/0171027 A1 | 9/2004 | Barnes et al. |
| 2005/0208506 A1 | 9/2005 | Zhao et al. |
| 2005/0283858 A1 | 12/2005 | Yao et al. |
| 2009/0013424 A1 | 1/2009 | Yao et al. |
| 2010/0115650 A1* | 5/2010 | Yao .......................... C12N 9/88 800/260 |

FOREIGN PATENT DOCUMENTS

| | | | |
|---|---|---|---|
| WO | WO 2008/124495 A2 | 10/2008 | |
| WO | WO 2009/031031 A2 | 3/2009 | |
| WO | WO 2009/046334 | * 4/2009 | ............... C12Q 1/68 |
| WO | WO 2009/046334 A1 | 4/2009 | |
| WO | WO 2010/037061 A1 | 4/2010 | |

OTHER PUBLICATIONS

Guo, Haiwei H., Juno Choe, and Lawrence A. Loeb. "Protein tolerance to random amino acid change." Proceedings of the National Academy of Sciences of the United States of America 101.25 (2004): 9205-9210.*
Beyond® herbicide label.*
Altschul et al., "Basic Local Alignment Search Tool", J. Mol. Biol., vol. 215, 1990, pp. 403-410.
Beyer et al., "Sulfonylureas", Herbicides: Chemistry, Degradation, and Mode of Action, 1998, pp. 117-189.
International Search Report, dated Jul. 18, 2012, for International Application No. PCT/EP2012/058239.
Jesske et al., "Brassica-Wildarten als neue genetische Ressource für die Rapszüchtung Wild species of Brassica as a new genetic resource for rapeseed breeding", Tagung der Vereinigung der Pflanzenzüchter und Saatgutkaufleute Österreichs, 2009, pp. 171-172, including English abstract.
Kleschick et al., "DE-498, a New Acetolactate Synthase Inhibiting Herbicide with Multicrop Selectivity", J. Agric. Food Chem., vol. 40, No. 6, 1992, pp. 1083-1085.
Murashige et al., "A Revised Medium for Rapid Growth and Bio Assays with Tobacco Tissue Cultures", Physiologia Plantarum, vol. 15, 1962, pp. 473-497.
Needleman et al., "A General Method Applicable to the Search for Similarities in the Amino Acid Sequence of Two Proteins", J. Mol. Biol., vol. 48, No. 3, 1970, pp. 443-453.
Pontzen, "Propoxycarbazone-sodium (BAY MKH 6561): systemic properties and basis of selectivity in wheat", Pflanzenschutz-Nachrichten Bayer, vol. 55, No. 1, 2002, pp. 37-52.
Ray, "Site of Action of Chlorsulfuron: Inhibition of Valine and Isoleucine Biosynthesis in Plants", Plant Physiol., vol. 75, 1984, pp. 827-831.
Rice et al., "EMBOSS: The European Molecular Biology Open Software Suite", TIG, vol. 16, No. 6, Jun. 2000, pp. 276-277.
Schmidt et al., "The physical and genomic organization of microsatellites in sugar beet", Proc. Natl. Acad. Sci. USA, vol. 93, Aug. 1996, pp. 8761-8765.
Shaner et al., "Imidazolinones: Potent Inhibitors of Acetohydroxyacid Synthase", Plant Physiol., vol. 76, 1984, pp. 545-546.
Shimizu et al., "Acetolactate Synthase Inhibitors", Herbicide Classes in Development, 2002, pp. 1-41.
Shimizu, "Action Mechanism of Pyrimidinyl Carboxy Herbicides", Pestic. Sci., vol. 22, 1997, pp. 245-256, including partial English translation.

(Continued)

*Primary Examiner* — Russell Kallis
*Assistant Examiner* — Fan Weihua
(74) *Attorney, Agent, or Firm* — Birch, Stewart, Kolasch & Birch, LLP

(57) ABSTRACT

The present invention relates to an ALS inhibitor herbicide tolerant *B. napus* plant, progeny and parts thereof comprising a non-transgenic mutation of an endogenous acetolactate synthase I gene and a non-transgenic mutation of an endogenous acetolactate synthase III gene.

20 Claims, 10 Drawing Sheets

(56) References Cited

OTHER PUBLICATIONS

Singh et al., "Assay of Acetohydroxyacid Synthase", Analytical Biochemistry, vol. 171, 1988, pp. 173-179.
Singh, "Biosynthesis of Valine, Leucine, and Isoleucine", Plant Amino Acids: Biochemistry and Biotechnology, 1999, pp. 227-247.
Tan et al., "Imidazolinone-tolerant crops: history, current status and future", Pest Management Science, vol. 61, 2005 (published online Dec. 31, 2004), pp. 246-257.
Tang et al., "Genetic variation of yellow-seeded rapeseed lines (Brassica napus L.) from different genetic sources", Plant Breeding, vol. 116, Oct. 1997, pp. 471-474.

Thompson et al., "CLUSTAL W: improving the sensitivity of progressive multiple sequence alignment through sequence weighting, position-specific gap penalties and weight matrix choice", Nucleic Acids Research, vol. 22, No. 22, 1994, pp. 4673-4680.
Hattori et al., "An acetohydroxy acid synthase mutant reveals a single site involved in multiple herbicide resistance", Mol Gen Genet 246, (1995), XP 002008914, pp. 419-425.
Kolkman et al., "Acetohydroxyacid synthase mutations conferring resistance to imidazolinone or sulfonylurea herbicides in sunflower", Theor Appl Genet 109, (2004), XP-002659976, pp. 1147-1159.
Tranel et al., "Resistance of weeds to ALS-inhibiting herbicides: what have we learned?", Weed Science, 50, XP009058814, (2002), pp. 700-712.

\* cited by examiner

Figure 1A

```
              1                                                  50
SEQ ID NO 9   (1)   ATGGCGGCGGCAACAACAACAACAACAACATCTTCTTCGATCTCCTTCTC
SEQ ID NO 5   (1)   ATGGCGGCGGCAACATCG------------TCTTCTCCGATCTCCTTAAC
SEQ ID NO 1   (1)   ATGGCGGCGGCAACATCG------------TCTTCTCCGATCTCCTTAAC
SEQ ID NO 3   (1)   ATGGCGGCGGCAACATCG------------TCTTCTCCGATCTCCTTAAC
SEQ ID NO 7   (1)   ATGGCGGCGGCAACATCG------------TCTTCTCCGATCTCCTTAAC
              51                                                 100
SEQ ID NO 9   (51)  CACCAAACCATCTCCTTCCTCCTCCAAATCACCATTACCAATCTCCAGAT
SEQ ID NO 5   (39)  CGCTAAACCTTC---T------TCCAAATCCCCTCTACCCATTTCCAGAT
SEQ ID NO 1   (39)  CGCTAAACCTTC---T------TCCAAATCCCCTCTACCCATTTCCAGAT
SEQ ID NO 3   (39)  CGCTAAACCTTC---T------TCCAAATCCCCTCTACCCATTTCCAGAT
SEQ ID NO 7   (39)  CGCTAAACCTTC---T------TCCAAATCCCCTCTACCCATTTCCAGAT
              101                                                150
SEQ ID NO 9   (101) TCTCCCTCCCATTCTCCCTAAACCCCAACAAATCATCCTCCTCCTCCCGC
SEQ ID NO 5   (80)  TCTCCCTTCCCTTCTCCTTAACCCCACAGAAAGA------CTCCTCCCGT
SEQ ID NO 1   (80)  TCTCCCTTCCCTTCTCCTTAACCCCACAGAAAGA------CTCCTCCCGT
SEQ ID NO 3   (80)  TCTCCCTTCCCTTCTCCTTAACCCCACAGAAACC------CTCCTCCCGT
SEQ ID NO 7   (80)  TCTCCCTTCCCTTCTCCTTAACCCCACAGAAACC------CTCCTCCCGT
              151                                                200
SEQ ID NO 9   (151) CGCCGCGGTATCAAATCCAGCTCTCCCTCCTCCATCTCCGCCGTGCTCAA
SEQ ID NO 5   (124) CTCCACCGTC----------CTCTC-----GCCATCTCCGCCGTTCTCAA
SEQ ID NO 1   (124) CTCCACCGTC----------CTCTC-----GCCATCTCCGCCGTTCTCAA
SEQ ID NO 3   (124) CTCCACCGTC----------CACTC-----GCCATCTCCGCCGTTCTCAA
SEQ ID NO 7   (124) CTCCACCGTC----------CTCTC-----GCCATCTCCGCCGTTCTCAA
              201                                                250
SEQ ID NO 9   (201) CACAACCACCAATGTGACAACCACTCCCTCTCCAACCAAACCTACCAAAC
SEQ ID NO 5   (159) CTCACCCGTCAATGTCGCACCTCCTTCCCCTGAAA--AAACCGACAAGAA
SEQ ID NO 1   (159) CTCACCCGTCAATGTCGCACCTCCTTCCCCTGAAA--AAACCGACAAGAA
SEQ ID NO 3   (159) CTCACCCGTCAATGTCGCA-CC------T--GAAA--AAACCGACAAGAT
SEQ ID NO 7   (159) CTCACCCGTCAATGTCGCA-CC------T--GAAA--AAACCGACAAGAT
              251                                                300
SEQ ID NO 9   (251) CCGAAACATTCATCTCCCGATTCGCTCCAGATCAACCCCGCAAAGGCGCT
SEQ ID NO 5   (207) CA-AGACTTTCGTCTCCCGCTACGCTCCCGACGAGCCCCGCAAGGGTGCT
SEQ ID NO 1   (207) CA-AGACTTTCGTCTCCCGCTACGCTCCCGACGAGCCCCGCAAGGGTGCT
SEQ ID NO 3   (198) CA-AGACTTTCATCTCCCGCTACGCTCCCGACGAGCCCCGCAAGGGTGCT
SEQ ID NO 7   (198) CA-AGACTTTCATCTCCCGCTACGCTCCCGACGAGCCCCGCAAGGGTGCT
              301                                                350
```

Figure 1B

```
SEQ ID NO 9  (301) GATATCCTCGTCGAAGCTTTAGAACGTCAAGGCGTAGAAACCGTATTCGC
SEQ ID NO 5  (256) GATATCCTCGTCGAAGCCCTCGAGCGTCAAGGCGTCGAAACCGTCTTTGC
SEQ ID NO 1  (256) GATATCCTCGTCGAAGCCCTCGAGCGTCAAGGCGTCGAAACCGTCTTTGC
SEQ ID NO 3  (247) GATATCCTCGTGGAAGCCCTCGAGCGTCAAGGCGTCGAAACCGTCTTCGC
SEQ ID NO 7  (247) GATATCCTCGTGGAAGCCCTCGAGCGTCAAGGCGTCGAAACCGTCTTCGC
                    351                                              400
SEQ ID NO 9  (351) TTACCCTGGAGGTGCATCAATGGAGATTCACCAAGCCTTAACCCGCTCTT
SEQ ID NO 5  (306) TTATCCCGGAGGTGCTTCCATGGAGATCCACCAAGCCTTGACTCGCTCCT
SEQ ID NO 1  (306) TTATCCCGGAGGTGCTTCCATGGAGATCCACCAAGCCTTGACTCGCTCCT
SEQ ID NO 3  (297) TTATCCCGGAGGTGCCTCCATGGAGATCCACCAAGCCTTGACTCGCTCCT
SEQ ID NO 7  (297) TTATCCCGGAGGTGCCTCCATGGAGATCCACCAAGCCTTGACTCGCTCCT
                    401                                              450
SEQ ID NO 9  (401) CCTCAATCCGTAACGTCCTTCCTCGTCACGAACAAGGAGGTGTATTCGCA
SEQ ID NO 5  (356) CCACCATCCGTAACGTCCTTCCCCGTCACGAACAAGGAGGAGTCTTCGCC
SEQ ID NO 1  (356) CCACCATCCGTAACGTCCTTCCCCGTCACGAACAAGGAGGAGTCTTCGCC
SEQ ID NO 3  (347) CCACCATCCGTAACGTCCTCCCCCGTCACGAACAAGGAGGAGTCTTCGCC
SEQ ID NO 7  (347) CCACCATCCGTAACGTCCTCCCCCGTCACGAACAAGGAGGAGTCTTCGCC
                    451                                              500
SEQ ID NO 9  (451) GCAGAAGGATACGCTCGATCCTCAGGTAAACCAGGTATCTGTATAGCCAC
SEQ ID NO 5  (406) GCCGAGGGTTACGCTCGTTCCTCCGGCAAACCGGGAATCTGCATAGCCAC
SEQ ID NO 1  (406) GCCGAGGGTTACGCTCGTTCCTCCGGCAAACCGGGAATCTGCATAGCCAC
SEQ ID NO 3  (397) GCCGAGGGTTACGCTCGTTCCTCCGGCAAACCGGGAATCTGCATAGCCAC
SEQ ID NO 7  (397) GCCGAGGGTTACGCTCGTTCCTCCGGCAAACCGGGAATCTGCATAGCCAC
                    501                                              550
SEQ ID NO 9  (501) TTCAGGTCCCGGAGCTACAAATCTCGTTAGCGGATTAGCCGATGCGTTGT
SEQ ID NO 5  (456) TTCGGGTCCCGGAGCTACCAACCTCGTCAGCGGGTTAGCAGACGCGATGC
SEQ ID NO 1  (456) TTCGGGTCCCGGAGCTACCAACCTCGTCAGCGGGTTAGCAGACGCGATGC
SEQ ID NO 3  (447) TTCGGGTCCCGGAGCTACCAACCTCGTCAGCGGGTTAGCCGACGCGATGC
SEQ ID NO 7  (447) TTCGGGTCCCGGAGCTACCAACCTCGTCAGCGGGTTAGCCGACGCGATGC
                    551                                              600
SEQ ID NO 9  (551) TAGATAGTGTTCCTCTTGTAGCAATCACAGGACAAGTCCCTCGTCGTATG
SEQ ID NO 5  (506) TTGACAGTGTTCCTCTTGTCGCCATTACAGGACAGGTCCCTCGCCGGATG
SEQ ID NO 1  (506) TTGACAGTGTTCCTCTTGTCGCCATTACAGGACAGGTCCCTCGCCGGATG
SEQ ID NO 3  (497) TTGACAGTGTTCCTCTCGTCGCCATCACAGGACAGGTCCCTCGCCGGATG
SEQ ID NO 7  (497) TTGACAGTGTTCCTCTCGTCGCCATCACAGGACAGGTCCCTCGCCGGATG
                    601                                              650
```

Figure 1C

```
SEQ ID NO 9   (601) ATTGGTACAGATGCGTTTCAAGAGACTCCGATTGTTGAGGTAACGCGTTC
SEQ ID NO 5   (556) ATCGGTACTGACGTCTTCCAAGAGACACCAATCGTTGAGGTAACGAGGTC
SEQ ID NO 1   (556) ATCGGTACTGACGCCTTCCAAGAGACACCAATCGTTGAGGTAACGAGGTC
SEQ ID NO 3   (547) ATCGGTACTGACGCGTTCCAAGAGACGCCAATCGTTGAGGTAACGAGGTC
SEQ ID NO 7   (547) ATCGGTACTGACGCCTTCCAAGAGACGCCAATCGTTGAGGTAACGAGGTC
                    651                                              700
SEQ ID NO 9   (651) GATTACGAAGCATAACTATCTTGTGATGGATGTTGAAGATATCCCTAGGA
SEQ ID NO 5   (606) TATTACGAAACATAACTATTTGGTGATGGATGTTGATGACATACCTAGGA
SEQ ID NO 1   (606) TATTACGAAACATAACTATTTGGTGATGGATGTTGATGACATACCTAGGA
SEQ ID NO 3   (597) TATTACGAAACATAACTATCTGGTGATGGATGTTGATGACATACCTAGGA
SEQ ID NO 7   (597) TATTACGAAACATAACTATCTGGTGATGGATGTTGATGACATACCTAGGA
                    701                                              750
SEQ ID NO 9   (701) TTATTGAGGAAGCTTTCTTTTTAGCTACTTCTGGTAGACCTGGACCTGTT
SEQ ID NO 5   (656) TCGTTCAAGAAGCTTTCTTTCTAGCTACTTCCGGTAGACCCGGACCGGTT
SEQ ID NO 1   (656) TCGTTCAAGAAGCTTTCTTTCTAGCTACTTCCGGTAGACCCGGACCGGTT
SEQ ID NO 3   (647) TCGTTCAAGAAGCATTCTTTCTAGCTACTTCCGGTAGACCCGGACCGGTT
SEQ ID NO 7   (647) TCGTTCAAGAAGCATTCTTTCTAGCTACTTCCGGTAGACCCGGACCGGTT
                    751                                              800
SEQ ID NO 9   (751) TTGGTTGATGTTCCTAAAGATATTCAACAACAGCTTGCGATTCCTAATTG
SEQ ID NO 5   (706) TTGGTTGATGTTCCTAAGGATATTCAGCAGCAGCTTGCGATTCCTAACTG
SEQ ID NO 1   (706) TTGGTTGATGTTCCTAAGGATATTCAGCAGCAGCTTGCGATTCCTAACTG
SEQ ID NO 3   (697) TTGGTTGATGTTCCTAAGGATATTCAGCAGCAGCTTGCGATTCCTAACTG
SEQ ID NO 7   (697) TTGGTTGATGTTCCTAAGGATATTCAGCAGCAGCTTGCGATTCCTAACTG
                    801                                              850
SEQ ID NO 9   (801) GGAACAGGCTATGAGATTACCTGGTTATATGTCTAGGATGCCTAAACCTC
SEQ ID NO 5   (756) GGATCAACCTATGCGCTTACCTGGCTACATGTCTAGGTTGCCTCAGCCTC
SEQ ID NO 1   (756) GGATCAACCTATGCGCTTACCTGGCTACATGTCTAGGTTGCCTCAGCCTC
SEQ ID NO 3   (747) GGATCAACCTATGCGCTTGCCTGGCTACATGTCTAGGCTGCCTCAGCCAC
SEQ ID NO 7   (747) GGATCAACCTATGCGCTTGCCTGGCTACATGTCTAGGCTGCCTCAGCCAC
                    851                                              900
SEQ ID NO 9   (851) CGGAAGATTCTCATTTGGAGCAGATTGTTAGGTTGATTTCTGAGTCTAAG
SEQ ID NO 5   (806) CGGAAGTTTCTCAGTTAGGTCAGATCGTTAGGTTGATCTCGGAGTCTAAG
SEQ ID NO 1   (806) CGGAAGTTTCTCAGTTAGGTCAGATCGTTAGGTTGATCTCGGAGTCTAAG
SEQ ID NO 3   (797) CGGAAGTTTCTCAGTTAGGCCAGATCGTTAGGTTGATCTCGGAGTCTAAG
SEQ ID NO 7   (797) CGGAAGTTTCTCAGTTAGGCCAGATCGTTAGGTTGATCTCGGAGTCTAAG
                    901                                              950
```

Figure 1D

```
SEQ ID NO 9   (901)  AAGCCTGTGTTGTATGTTGGTGGTGGTTGTTTGAATTCTAGCGATGAATT
SEQ ID NO 5   (856)  AGGCCTGTTTTGTACGTTGGTGGTGGAAGCTTGAACTCGAGTGAAGAACT
SEQ ID NO 1   (856)  AGGCCTGTTTTGTACGTTGGTGGTGGAAGCTTGAACTCGAGTGAAGAACT
SEQ ID NO 3   (847)  AGGCCTGTTTTGTACGTTGGTGGTGGAAGCTTGAACTCGAGTGAAGAACT
SEQ ID NO 7   (847)  AGGCCTGTTTTGTACGTTGGTGGTGGAAGCTTGAACTCGAGTGAAGAACT
                     951                                              1000
SEQ ID NO 9   (951)  GGGTAGGTTTGTTGAGCTTACGGGGATCCCTGTTGCGAGTACGTTGATGG
SEQ ID NO 5   (906)  GGGGAGATTTGTCGAGCTTACTGGGATCCCCGTTGCGAGTACTTTGATGG
SEQ ID NO 1   (906)  GGGGAGATTTGTCGAGCTTACTGGGATCCCCGTTGCGAGTACTTTGATGG
SEQ ID NO 3   (897)  GGGGAGATTTGTCGAGCTTACTGGGATCCCTGTTGCGAGTACGTTGATGG
SEQ ID NO 7   (897)  GGGGAGATTTGTCGAGCTTACTGGGATCCCTGTTGCGAGTACGTTGATGG
                     1001                                             1050
SEQ ID NO 9   (1001) GGCTGGGATCTTATCCTTGTGATGATGAGTTGTCGTTACATATGCTTGGA
SEQ ID NO 5   (956)  GGCTTGGCTCTTATCCTTGTAACGATGAGTTGTCCCTGCAGATGCTTGGC
SEQ ID NO 1   (956)  GGCTTGGCTCTTATCCTTGTAACGATGAGTTGTCCCTGCAGATGCTTGGC
SEQ ID NO 3   (947)  GGCTTGGCTCTTATCCTTGTAACGATGAGTTGTCCCTGCAGATGCTTGGC
SEQ ID NO 7   (947)  GGCTTGGCTCTTATCCTTGTAACGATGAGTTGTCCCTGCAGATGCTTGGC
                     1051                                             1100
SEQ ID NO 9   (1051) ATGCATGGGACTGTGTATGCAAATTACGCTGTGGAGCATAGTGATTTGTT
SEQ ID NO 5   (1006) ATGCACGGGACTGTGTATGCTAACTACGCTGTGGAGCATAGTGATTTGTT
SEQ ID NO 1   (1006) ATGCACGGGACTGTGTATGCTAACTACGCTGTGGAGCATAGTGATTTGTT
SEQ ID NO 3   (997)  ATGCACGGGACTGTGTATGCTAACTACGCTGTGGAGCATAGTGATTTGTT
SEQ ID NO 7   (997)  ATGCACGGGACTGTGTATGCTAACTACGCTGTGGAGCATAGTGATTTGTT
                     1101                                             1150
SEQ ID NO 9   (1101) GTTGGCGTTTGGGGTAAGGTTTGATGATCGTGTCACGGGTAAGCTTGAGG
SEQ ID NO 5   (1056) GCTGGCGTTTGGTGTTAGGTTTGATGACCGTGTCACGGGAAAGCTCGAGG
SEQ ID NO 1   (1056) GCTGGCGTTTGGTGTTAGGTTTGATGACCGTGTCACGGGAAAGCTCGAGG
SEQ ID NO 3   (1047) GCTGGCGTTTGGTGTTAGGTTTGATGACCGTGTCACGGGAAAGCTCGAGG
SEQ ID NO 7   (1047) GCTGGCGTTTGGTGTTAGGTTTGATGACCGTGTCACGGGAAAGCTCGAGG
                     1151                                             1200
SEQ ID NO 9   (1151) CTTTTGCTAGTAGGGCTAAGATTGTTCATATTGATATTGACTCGGCTGAG
SEQ ID NO 5   (1106) CTTTCGCTAGCAGGGCTAAAATTGTGCACATAGACATTGATTCTGCTGAG
SEQ ID NO 1   (1106) CTTTCGCTAGCAGGGCTAAAATTGTGCACATAGACATTGATTCTGCTGAG
SEQ ID NO 3   (1097) CGTTTGCGAGCAGGGCTAAGATTGTGCACATAGACATTGATTCTGCTGAG
SEQ ID NO 7   (1097) CGTTTGCGAGCAGGGCTAAGATTGTGCACATAGACATTGATTCTGCTGAG
                     1201                                             1250
```

Figure 1E

```
SEQ ID NO 9  (1201)  ATTGGGAAGAATAAGACTCCTCATGTGTCTGTGTGTGGTGATGTTAAGCT
SEQ ID NO 5  (1156)  ATTGGGAAGAATAAGACACCTCACGTGTCTGTGTGTGGTGATGTAAAGCT
SEQ ID NO 1  (1156)  ATTGGGAAGAATAAGACACCTCACGTGTCTGTGTGTGGTGATGTAAAGCT
SEQ ID NO 3  (1147)  ATTGGGAAGAATAAGACACCTCACGTGTCTGTGTGTGGTGATGTAAAGCT
SEQ ID NO 7  (1147)  ATTGGGAAGAATAAGACACCTCACGTGTCTGTGTGTGGTGATGTAAAGCT
                     1251                                           1300
SEQ ID NO 9  (1251)  GGCTTTGCAAGGGATGAATAAGGTTCTTGAGAACCGAGCGGAGGAGCTTA
SEQ ID NO 5  (1206)  GGCTTTGCAAGGGATGAACAAGGTTCTTGAGAACCGGGCGGAGGAGCTCA
SEQ ID NO 1  (1206)  GGCTTTGCAAGGGATGAACAAGGTTCTTGAGAACCGGGCGGAGGAGCTCA
SEQ ID NO 3  (1197)  GGCTTTGCAAGGGATGAACAAGGTTCTTGAGAACCGGGCGGAGGAGCTCA
SEQ ID NO 7  (1197)  GGCTTTGCAAGGGATGAACAAGGTTCTTGAGAACCGGGCGGAGGAGCTCA
                     1301                                           1350
SEQ ID NO 9  (1301)  AGCTTGATTTTGGAGTTTGGAGGAATGAGTTGAACGTACAGAAACAGAAG
SEQ ID NO 5  (1256)  AGCTTGATTTCGGTGTTTGGAGGAGTGAGTTGAGCGAGCAGAAACAGAAG
SEQ ID NO 1  (1256)  AGCTTGATTTCGGTGTTTGGAGGAGTGAGTTGAGCGAGCAGAAACAGAAG
SEQ ID NO 3  (1247)  AGCTTGATTTCGGTGTTTGGAGGAGTGAGTTGAGCGAGCAGAAACAGAAG
SEQ ID NO 7  (1247)  AGCTTGATTTCGGTGTTTGGAGGAGTGAGTTGAGCGAGCAGAAACAGAAG
                     1351                                           1400
SEQ ID NO 9  (1351)  TTTCCGTTGAGCTTTAAGACGTTTGGGGAAGCTATTCCTCCACAGTATGC
SEQ ID NO 5  (1306)  TTCCCTTTGAGCTTCAAAACGTTTGGAGAAGCCATTCCTCCGCAGTACGC
SEQ ID NO 1  (1306)  TTCCCTTTGAGCTTCAAAACGTTTGGAGAAGCCATTCCTCCGCAGTACGC
SEQ ID NO 3  (1297)  TTCCCGTTGAGCTTCAAAACGTTTGGAGAAGCCATTCCTCCGCAGTACGC
SEQ ID NO 7  (1297)  TTCCCGTTGAGCTTCAAAACGTTTGGAGAAGCCATTCCTCCGCAGTACGC
                     1401                                           1450
SEQ ID NO 9  (1401)  GATTAAGGTCCTTGATGAGTTGACTGATGGAAAAGCCATAATAAGTACTG
SEQ ID NO 5  (1356)  GATTCAGATCCTCGACGAGCTAACCGAAGGAAGGCAATTATCAGTACTG
SEQ ID NO 1  (1356)  GATTCAGATCCTCGACGAGCTAACCGAAGGAAGGCAATTATCAGTACTG
SEQ ID NO 3  (1347)  GATTCAGGTCCTAGACGAGCTAACCCAAGGGAAGGCAATTATCAGTACTG
SEQ ID NO 7  (1347)  GATTCAGGTCCTAGACGAGCTAACCCAAGGGAAGGCAATTATCAGTACTG
                     1451                                           1500
SEQ ID NO 9  (1451)  GTGTCGGGCAACATCAAATGTGGGCGGCGCAGTTCTACAATTACAAGAAA
SEQ ID NO 5  (1406)  GTGTTGGACAGCATCAGATGTGGGCGGCGCAGTTTTACAAGTACAGGAAG
SEQ ID NO 1  (1406)  GTGTTGGACAGCATCAGATGTGGGCGGCGCAGTTTTACAAGTACAGGAAG
SEQ ID NO 3  (1397)  GTGTTGGACAGCATCAGATGTGGGCGGCGCAGTTTTACAAGTACAGGAAG
SEQ ID NO 7  (1397)  GTGTTGGACAGCATCAGATGTGGGCGGCGCAGTTTTACAAGTACAGGAAG
                     1501                                           1550
```

Figure 1F

```
SEQ ID NO 9  (1501)  CCAAGGCAGTGGCTATCATCAGGAGGCCTTGGAGCTATGGGATTTGGACT
SEQ ID NO 5  (1456)  CCGAGACAGTGGCTGTCGTCATCAGGCCTCGGAGCTATGGGTTTTGGACT
SEQ ID NO 1  (1456)  CCGAGACAGTGGCTGTCGTCATCAGGCCTCGGAGCTATGGGTTTTGGACT
SEQ ID NO 3  (1447)  CCGAGGCAGTGGCTGTCGTCCTCAGGACTCGGAGCTATGGGTTTCGGACT
SEQ ID NO 7  (1447)  CCGAGGCAGTGGCTGTCGTCCTCAGGACTCGGAGCTATGGGTTTCGGACT
                     1551                                           1600
SEQ ID NO 9  (1551)  TCCTGCTGCGATTGGAGCGTCTGTTGCTAACCCTGATGCGATAGTTGTGG
SEQ ID NO 5  (1506)  TCCTGCTGCGATTGGAGCGTCTGTGGCGAACCCTGATGCGATTGTTGTGG
SEQ ID NO 1  (1506)  TCCTGCTGCGATTGGAGCGTCTGTGGCGAACCCTGATGCGATTGTTGTGG
SEQ ID NO 3  (1497)  TCCTGCTGCGATTGGAGCGTCTGTGGCGAACCCTGATGCGATTGTTGTGG
SEQ ID NO 7  (1497)  TCCTGCTGCGATTGGAGCGTCTGTGGCGAACCCTGATGCGATTGTTGTGG
                     1601                                           1650
SEQ ID NO 9  (1601)  ATATTGACGGAGATGGAAGCTTTATAATGAATGTGCAAGAGCTAGCCACT
SEQ ID NO 5  (1556)  ATATTGACGGTGATGGAAGCTTCATAATGAACGTTCAAGAGCTGGCCACA
SEQ ID NO 1  (1556)  ATATTGACGGTGATGGAAGCTTCATAATGAACGTTCAAGAGCTGGCCACA
SEQ ID NO 3  (1547)  ACATTGACGGTGATGGAAGCTTCATAATGAACGTTCAAGAGCTGGCCACA
SEQ ID NO 7  (1547)  ACATTGACGGTGATGGAAGCTTCATAATGAACGTTCAAGAGCTGGCCACA
                     1651                                           1700
SEQ ID NO 9  (1651)  ATTCGTGTAGAGAATCTTCCAGTGAAGGTACTTTTATTAAACAACCAGCA
SEQ ID NO 5  (1606)  ATCCGTGTAGAGAATCTTCCTGTGAAGATACTCTTGTTAAACAACCAGCA
SEQ ID NO 1  (1606)  ATCCGTGTAGAGAATCTTCCTGTGAAGATACTCTTGTTAAACAACCAGCA
SEQ ID NO 3  (1597)  ATCCGTGTAGAGAATCTTCCTGTGAAGATACTCTTGTTAAACAACCAGCA
SEQ ID NO 7  (1597)  ATCCGTGTAGAGAATCTTCCTGTGAAGATACTCTTGTTAAACAACCAGCA
                     1701                                           1750
SEQ ID NO 9  (1701)  TCTTGGCATGGTTATGCAATGGCAAGATCGGTTCTACAAAGCTAACCGAG
SEQ ID NO 5  (1656)  TCTTGGGATGGTCATGCAATGGGAAGATCGGTTCTACAAAGCTAACAGAG
SEQ ID NO 1  (1656)  TCTTGGGATGGTCATGCAATGGGAAGATCGGTTCTACAAAGCTAACAGAG
SEQ ID NO 3  (1647)  TCTTGGGATGGTCATGCAATGGGAAGATCGGTTCTACAAAGCTAACAGAG
SEQ ID NO 7  (1647)  TCTTGGGATGGTCATGCAA**TT̲G**GAAGATCGGTTCTACAAAGCTAACAGAG
                     1751                                           1800
SEQ ID NO 9  (1751)  CTCACACATTTCTCGGGGATCCGGCTCAGGAGGACGAGATATTCCCGAAC
SEQ ID NO 5  (1706)  CTCACACTTATCTCGGGGACCCGGCAAGGGAGAACGAGATCTTCCCTAAC
SEQ ID NO 1  (1706)  CTCACACTTATCTCGGGGACCCGGCAAGGGAGAACGAGATCTTCCCTAAC
SEQ ID NO 3  (1697)  CTCACACTTATCTCGGGGACCCGGCAAGGGAGAACGAGATCTTCCCTAAC
SEQ ID NO 7  (1697)  CTCACACTTATCTCGGGGACCCGGCAAGGGAGAACGAGATCTTCCCTAAC
                     1801                                           1850
```

Figure 1G

```
SEQ ID NO 9  (1801)  ATGTTGCTGTTTGCAGCAGCTTGCGGGATTCCAGCGGCGAGGGTGACAAA
SEQ ID NO 5  (1756)  ATGCTGCAGTTTGCAGGAGCTTGCGGGATTCCAGCTGCGAGAGTGACGAA
SEQ ID NO 1  (1756)  ATGCTGCAGTTTGCAGGAGCTTGCGGGATTCCAGCTGCGAGAGTGACGAA
SEQ ID NO 3  (1747)  ATGCTGCAGTTTGCAGGAGCTTGCGGGATTCCAGCTGCGAGAGTGACGAA
SEQ ID NO 7  (1747)  ATGCTGCAGTTTGCAGGAGCTTGCGGGATTCCAGCTGCGAGAGTGACGAA
                            1851                                          1900
SEQ ID NO 9  (1851)  GAAAGCAGATCTCCGAGAAGCTATTCAGACAATGCTGGATACACCAGGAC
SEQ ID NO 5  (1806)  GAAAGAAGAACTCCGAGAAGCTATTCAGACAATGCTGGATACACCAGGAC
SEQ ID NO 1  (1806)  GAAAGAAGAACTCCGAGAAGCTATTCAGACAATGCTGGATACACCAGGAC
SEQ ID NO 3  (1797)  GAAAGAAGAACTCCGAGAAGCTATTCAGACAATGCTGGATACACCTGGAC
SEQ ID NO 7  (1797)  GAAAGAAGAACTCCGAGAAGCTATTCAGACAATGCTGGATACACCTGGAC
                            1901                                          1950
SEQ ID NO 9  (1901)  CTTACCTGTTGGATGTGATTTGTCCGCACCAAGAACATGTGTTGCCGATG
SEQ ID NO 5  (1856)  CATACCTGTTGGATGTGATATGTCCGCACCAAGAACATGTGTTACCGATG
SEQ ID NO 1  (1856)  CATACCTGTTGGATGTGATATGTCCGCACCAAGAACATGTGTTACCGATG
SEQ ID NO 3  (1847)  CGTACCTGTTGGATGTCATCTGTCCGCACCAAGAACATGTGTTACCGATG
SEQ ID NO 7  (1847)  CGTACCTGTTGGATGTCATCTGTCCGCACCAAGAACATGTGTTACCGATG
                            1951                                          2000
SEQ ID NO 9  (1951)  ATCCCGAGTGGTGGCACTTTCAACGATGTCATAACGGAAGGAGATGGCCG
SEQ ID NO 5  (1906)  ATCCCAAGTGGTGGCACTTTCAAAGATGTAATAACAGAAGGGGATGGTCG
SEQ ID NO 1  (1906)  ATCCCAAGTGGTGGCACTTTCAAAGATGTAATAACAGAAGGGGATGGTCG
SEQ ID NO 3  (1897)  ATCCCAAGTGGTGGCACTTTCAAAGATGTAATAACCGAAGGGGATGGTCG
SEQ ID NO 7  (1897)  ATCCCAAGTGGTGGCACTTTCAAAGATGTAATAACCGAAGGGGATGGTCG
                            2001      2013
SEQ ID NO 9  (2001)  GATTAAATACTGA
SEQ ID NO 5  (1956)  CACTAAGTACTGA
SEQ ID NO 1  (1956)  CACTAAGTACTGA
SEQ ID NO 3  (1947)  CACTAAGTACTGA
SEQ ID NO 7  (1947)  CACTAAGTACTGA
```

Figure 2A

```
                      1                                                  50
SEQ ID NO 10    (1)   MAAATTTTTTSSSISFSTKPSPSSSKSPLPISRFSLPFSLNPNKSSSSSR
SEQ ID NO 2     (1)   ----MAAATSSSPISLTAKPS---SKSPLPISRFSLPFSLTPQKDSSRLH
SEQ ID NO 6     (1)   ----MAAATSSSPISLTAKPS---SKSPLPISRFSLPFSLTPQKDSSRLH
SEQ ID NO 4     (1)   ----MAAATSSSPISLTAKPS---SKSPLPISRFSLPFSLTPQKPSSRLH
SEQ ID NO 8     (1)   ----MAAATSSSPISLTAKPS---SKSPLPISRFSLPFSLTPQKPSSRLH
                      51                                                 100
SEQ ID NO 10   (51)   RRGIKSSSPSSISAVLNTTTNVTTTPSPTKPTKPETFISRFAPDQPRKGA
SEQ ID NO 2    (44)   R-------PLAISAVLNSPVNVAP-PSPEKTDKNKTFVSRYAPDEPRKGA
SEQ ID NO 6    (44)   R-------PLAISAVLNSPVNVAP-PSPEKTDKNKTFVSRYAPDEPRKGA
SEQ ID NO 4    (44)   R-------PLAISAVLNSPVNVAP----EKTDKIKTFISRYAPDEPRKGA
SEQ ID NO 8    (44)   R-------PLAISAVLNSPVNVAP----EKTDKIKTFISRYAPDEPRKGA
                      101                                                150
SEQ ID NO 10  (101)   DILVEALERQGVETVFAYPGGASMEIHQALTRSSSIRNVLPRHEQGGVFA
SEQ ID NO 2    (86)   DILVEALERQGVETVFAYPGGASMEIHQALTRSSTIRNVLPRHEQGGVFA
SEQ ID NO 6    (86)   DILVEALERQGVETVFAYPGGASMEIHQALTRSSTIRNVLPRHEQGGVFA
SEQ ID NO 4    (83)   DILVEALERQGVETVFAYPGGASMEIHQALTRSSTIRNVLPRHEQGGVFA
SEQ ID NO 8    (83)   DILVEALERQGVETVFAYPGGASMEIHQALTRSSTIRNVLPRHEQGGVFA
                      151                                                200
SEQ ID NO 10  (151)   AEGYARSSGKPGICIATSGPGATNLVSGLADALLDSVPLVAITGQVPRRM
SEQ ID NO 2   (136)   AEGYARSSGKPGICIATSGPGATNLVSGLADAMLDSVPLVAITGQVPRRM
SEQ ID NO 6   (136)   AEGYARSSGKPGICIATSGPGATNLVSGLADAMLDSVPLVAITGQVPRRM
SEQ ID NO 4   (133)   AEGYARSSGKPGICIATSGPGATNLVSGLADAMLDSVPLVAITGQVPRRM
SEQ ID NO 8   (133)   AEGYARSSGKPGICIATSGPGATNLVSGLADAMLDSVPLVAITGQVPRRM
                      201                                                250
SEQ ID NO 10  (201)   IGTDAFQETPIVEVTRSITKHNYLVMDVEDIPRIIEEAFFLATSGRPGPV
SEQ ID NO 2   (186)   IGTDAFQETPIVEVTRSITKHNYLVMDVDDIPRIVQEAFFLATSGRPGPV
SEQ ID NO 6   (186)   IGTDVFQETPIVEVTRSITKHNYLVMDVDDIPRIVQEAFFLATSGRPGPV
SEQ ID NO 4   (183)   IGTDAFQETPIVEVTRSITKHNYLVMDVDDIPRIVQEAFFLATSGRPGPV
SEQ ID NO 8   (183)   IGTDAFQETPIVEVTRSITKHNYLVMDVDDIPRIVQEAFFLATSGRPGPV 251                                                300
SEQ ID NO 10  (251)   LVDVPKDIQQQLAIPNWEQAMRLPGYMSRMPKPPEDSHLEQIVRLISESK
SEQ ID NO 2   (236)   LVDVPKDIQQQLAIPNWDQPMRLPGYMSRLPQPPEVSQLGQIVRLISESK
```

Figure 2B

```
SEQ ID NO 6   (236) LVDVPKDIQQQLAIPNWDQPMRLPGYMSRLPQPPEVSQLGQIVRLISESK
SEQ ID NO 4   (233) LVDVPKDIQQQLAIPNWDQPMRLPGYMSRLPQPPEVSQLGQIVRLISESK
SEQ ID NO 8   (233) LVDVPKDIQQQLAIPNWDQPMRLPGYMSRLPQPPEVSQLGQIVRLISESK
                    301                                              350
SEQ ID NO 10  (301) KPVLYVGGGCLNSSDELGRFVELTGIPVASTLMGLGSYPCDDELSLHMLG
SEQ ID NO 2   (286) RPVLYVGGGSLNSSEELGRFVELTGIPVASTLMGLGSYPCNDELSLQMLG
SEQ ID NO 6   (286) RPVLYVGGGSLNSSEELGRFVELTGIPVASTLMGLGSYPCNDELSLQMLG
SEQ ID NO 4   (283) RPVLYVGGGSLNSSEELGRFVELTGIPVASTLMGLGSYPCNDELSLQMLG
SEQ ID NO 8   (283) RPVLYVGGGSLNSSEELGRFVELTGIPVASTLMGLGSYPCNDELSLQMLG
                    351                                              400
SEQ ID NO 10  (351) MHGTVYANYAVEHSDLLLAFGVRFDDRVTGKLEAFASRAKIVHIDIDSAE
SEQ ID NO 2   (336) MHGTVYANYAVEHSDLLLAFGVRFDDRVTGKLEAFASRAKIVHIDIDSAE
SEQ ID NO 6   (336) MHGTVYANYAVEHSDLLLAFGVRFDDRVTGKLEAFASRAKIVHIDIDSAE
SEQ ID NO 4   (333) MHGTVYANYAVEHSDLLLAFGVRFDDRVTGKLEAFASRAKIVHIDIDSAE
SEQ ID NO 8   (333) MHGTVYANYAVEHSDLLLAFGVRFDDRVTGKLEAFASRAKIVHIDIDSAE
                    401                                              450
SEQ ID NO 10  (401) IGKNKTPHVSVCGDVKLALQGMNKVLENRAEELKLDFGVWRNELNVQKQK
SEQ ID NO 2   (386) IGKNKTPHVSVCGDVKLALQGMNKVLENRAEELKLDFGVWRSELSEQKQK
SEQ ID NO 6   (386) IGKNKTPHVSVCGDVKLALQGMNKVLENRAEELKLDFGVWRSELSEQKQK
SEQ ID NO 4   (383) IGKNKTPHVSVCGDVKLALQGMNKVLENRAEELKLDFGVWRSELSEQKQK
SEQ ID NO 8   (383) IGKNKTPHVSVCGDVKLALQGMNKVLENRAEELKLDFGVWRSELSEQKQK
                    451                                              500
SEQ ID NO 10  (451) FPLSFKTFGEAIPPQYAIKVLDELTDGKAIISTGVGQHQMWAAQFYNYKK
SEQ ID NO 2   (436) FPLSFKTFGEAIPPQYAIQILDELTEGKAIISTGVGQHQMWAAQFYKYRK
SEQ ID NO 6   (436) FPLSFKTFGEAIPPQYAIQILDELTEGKAIISTGVGQHQMWAAQFYKYRK
SEQ ID NO 4   (433) FPLSFKTFGEAIPPQYAIQVLDELTQGKAIISTGVGQHQMWAAQFYKYRK
SEQ ID NO 8   (433) FPLSFKTFGEAIPPQYAIQVLDELTQGKAIISTGVGQHQMWAAQFYKYRK
                    501                                              550
SEQ ID NO 10  (501) PRQWLSSGGLGAMGFGLPAAIGASVANPDAIVVDIDGDGSFIMNVQELAT
SEQ ID NO 2   (486) PRQWLSSSGLGAMGFGLPAAIGASVANPDAIVVDIDGDGSFIMNVQELAT
SEQ ID NO 6   (486) PRQWLSSSGLGAMGFGLPAAIGASVANPDAIVVDIDGDGSFIMNVQELAT
SEQ ID NO 4   (483) PRQWLSSSGLGAMGFGLPAAIGASVANPDAIVVDIDGDGSFIMNVQELAT
SEQ ID NO 8   (483) PRQWLSSSGLGAMGFGLPAAIGASVANPDAIVVDIDGDGSFIMNVQELAT
                    551                                              600
SEQ ID NO 10  (551) IRVENLPVKVLLLNNQHLGMVMQWQDRFYKANRAHTFLGDPAQEDEIFPN
SEQ ID NO 2   (536) IRVENLPVKILLLNNQHLGMVMQWEDRFYKANRAHTYLGDPARENEIFPN
SEQ ID NO 6   (536) IRVENLPVKILLLNNQHLGMVMQWEDRFYKANRAHTYLGDPARENEIFPN
SEQ ID NO 4   (533) IRVENLPVKILLLNNQHLGMVMQWEDRFYKANRAHTYLGDPARENEIFPN
SEQ ID NO 8   (533) IRVENLPVKILLLNNQHLGMVMQLEDRFYKANRAHTYLGDPARENEIFPN
                    601                                              650
```

Figure 2C

```
SEQ ID NO 10   (601)  MLLFAAACGIPAARVTKKADLREAIQTMLDTPGPYLLDVICPHQEHVLPM
SEQ ID NO 2    (586)  MLQFAGACGIPAARVTKKEELREAIQTMLDTPGPYLLDVICPHQEHVLPM
SEQ ID NO 6    (586)  MLQFAGACGIPAARVTKKEELREAIQTMLDTPGPYLLDVICPHQEHVLPM
SEQ ID NO 4    (583)  MLQFAGACGIPAARVTKKEELREAIQTMLDTPGPYLLDVICPHQEHVLPM
SEQ ID NO 8    (583)  MLQFAGACGIPAARVTKKEELREAIQTMLDTPGPYLLDVICPHQEHVLPM
                             651            670
SEQ ID NO 10   (651)  IPSGGTFNDVITEGDGRIKY
SEQ ID NO 2    (636)  IPSGGTFKDVITEGDGRTKY
SEQ ID NO 6    (636)  IPSGGTFKDVITEGDGRTKY
SEQ ID NO 4    (633)  IPSGGTFKDVITEGDGRTKY
SEQ ID NO 8    (633)  IPSGGTFKDVITEGDGRTKY
```

ALS INHIBITOR HERBICIDE TOLERANT *B. NAPUS* MUTANTS

CROSS REFERENCE TO RELATED APPLICATIONS

This application is the National Phase of PCT/EP2012/058239 filed on May 4, 2012, which claims priority under 35 U.S.C. 119(e) to U.S. Provisional Application No. 61/482,287 filed on May 4, 2011, and under 35 U.S.C 119(a) to patent application Ser. No. 11/164,720.2 filed in the European Patent Office on May 4, 2011, all of which are hereby expressly incorporated by reference into the present application.

This invention relates to herbicide-resistant *Brassica napus* plants, seed of such plants, parts thereof, progeny thereof as well as a method for their manufacture, and methods using such plants.

WO09/046334 describes mutated acetohydroxyacid synthase (AHAS) nucleic acids and the proteins encoded by the mutated nucleic acids, as well as canola plants, cells, and seeds comprising the mutated genes, whereby the plants display increased tolerance to imidazolinones and sulfonylureas.

WO09/031031 discloses herbicide-resistant *Brassica* plants and novel polynucleotide sequences that encode wild-type and imidazolinane-resistant *Brassica* acetohydroxyacid synthase large subunit proteins, seeds, and methods using such plants.

US 09/0013424 describes improved imidazolinone herbicide resistant *Brassica* lines, including *Brassica juncea*, methods for generation of such lines, and methods for selection of such lines, as well as *Brassica* AHAS genes and sequences and a gene allele bearing a point mutation that gives rise to imidazolinone herbicide resistance.

WO 08/124495 discloses nucleic acids encoding mutants of the acetohydroxyacid synthase (AHAS) large subunit comprising at least two mutations, for example double and triple mutants, which are useful for producing transgenic or non-transgenic plants with improved levels of tolerance to AHAS-inhibiting herbicides. The invention also provides expression vectors, cells, plants comprising the polynucleotides encoding the AHAS large subunit double and triple mutants, plants comprising two or more AHAS large subunit single mutant polypeptides, and methods for making and using the same.

WO 2010/037061 describes transgenic and non-transgenic plants with improved tolerance to AHAS-inhibiting herbicides.

Tan et al. (2005, Pest. Manag. Sci 61: 246-257) inter alfa refers to imidazolinone-tolerant oilseed rape.

Acetohydroxyacid synthase (AHAS), also known as "acetolactate synthase" (ALS [EC 4.1.3.18]) is the first enzyme that catalyzes the biochemical synthesis of the branched chain amino acids valine, leucine and isoleucine (Singh (1999) "Biosynthesis of valine, leucine and isoleucine," in Plant Amino Acid, Singh, B. K., ed., Marcel Dekker Inc. New York, N.Y., pp. 227-247).

Some chemicals inhibit ALS which is the site of action of five structurally diverse herbicide families belonging to the class of ALS inhibitor herbicides, like (a) sulfonylurea herbicides (Beyer E. M et al. (1988), Sulfonylureas in Herbicides: Chemistry, Degradation, and Mode of Action; Marcel Dekker, New York, 1988, 117-189), (b) sulfonylaminocarbonyltriazolinone herbicides (Pontzen, R., Pflanz.-Nachrichten Bayer, 2002, 55, 37-52), (c) imidazolinone herbicides (Shaner, D. L., et al., Plant Physiol., 1984, 76, 545-546; Shaner, D. L., and O'Connor, S. L. (Eds.) The Imidazolinone Herbicides, CRC Press, Boca Raton, Fla., 1991), (d) triazolopyrimidine herbicides (Kleschick, W. A. et al., Agric. Food Chem., 1992, 40, 1083-1085), and (e) pyrimidinyl(thio)benzoate herbicides (Shimizu, T. J., Pestic. Sci., 1997, 22, 245-256; Shimizu, T. et al., Acetolactate Synthetase Inhibitors in Herbicide Classes in Development. Böger, P., Wakabayashi, K., Hirai, K., (Eds.), Springer Verlag, Berlin, 2002, 1-41).

Inhibitors of the ALS interrupt the biosynthesis of valine, leucine and isoleucine in plants. The consequence is an immediate depletion of the respective amino acid pools causing a stop of protein biosynthesis leading to a cessation of plant growth and eventually the plant dies, or—at least—is damaged.

ALS inhibitor herbicides such as imidazolinone and sulfonylurea herbicides are widely used in modern agriculture due to their effectiveness at moderate application rates and relative non-toxicity in animals. By inhibiting ALS activity, these families of herbicides prevent further growth and development of susceptible plants including many weed species. In order to provide plants with an increased tolerance to even high concentrations of ALS inhibitor herbicides that may be required for sufficient weed control, additional ALS-inhibiting herbicide-resistant breeding lines and varieties of crop plants, as well as methods and compositions for the production and use of ALS inhibiting herbicide-resistant breeding lines and varieties, are needed.

Thus, the technical problem is to comply with this need.

The present invention addresses this need and thus provides as a solution to the technical problem an herbicide tolerant *Brassica napus* (*B. napus*) plant and parts thereof according to the present invention.

By applying various breeding methods, high yielding commercial varieties highly competitive in all specific markets with the add-on of a robust ALS inhibitor herbicide tolerance can be developed subsequently by using the originally obtained mutant plants.

SUMMARY OF THE INVENTION

In one aspect, the present invention provides an ALS inhibitor herbicide tolerant *B. napus* plant or parts thereof comprising an ALS I polypeptide comprising an amino acid different from alanine at a position of said ALS I polypeptide corresponding to position 190 of SEQ ID NO: 2 and an ALS III polypeptide comprising an amino acid different from tryptophan at a position of said ALS III polypeptide corresponding to position 556 of SEQ ID NO: 4.

In one embodiment, said plant comprises non-transgenic mutations of its endogenous acetolactate synthase (ALS) genes, wherein an ALS gene I encodes an ALS I polypeptide comprising an amino acid different from alanine at a position of said ALS I polypeptide corresponding to position 190 of SEQ ID NO: 2 (this position corresponds to position 205 of the *A. thaliana* SEQ ID NO: 10) and wherein an ALS III gene encodes an ALS III polypeptide comprising an amino acid different from tryptophan at a position of said ALS III polypeptide corresponding to position 556 of SEQ ID NO: 4 (this position corresponds to position 574 of the *A. thaliana* SEQ ID NO: 10).

In another embodiment, said ALS I polypeptide in said plant or parts thereof has at a position corresponding to position 190 of SEQ ID NO: 2 instead of the naturally encoded amino acid alanine an amino acid selected from the group consisting of tryptophan (W), valine (V), methionine (M), isoleucine (I), leucine (L), proline (P), phenylalanine (F), arginine (R), lysine (K), histidine (H), aspartate (D), cysteine (C), glutamate (E), glycine (G), serine (S), threonine (T), tyrosine (Y) and glutamine (Q) and asparagine (N) and said ALS III polypeptide in said plant or parts thereof has at a position corresponding to position 556 of SEQ ID NO: 4 instead of the naturally encoded amino acid tryptophan an amino acid selected from the group consisting of alanine (A), valine (V), methionine (M), isoleucine (I), leucine (L), proline (P), phenylalanine (F), arginine (R), lysine (K), histidine (H), aspartate (D), cysteine (C), glutamate (E), glycine (G), serine (S), threonine (T), tyrosine (Y) and glutamine (Q) and asparagine (N).

In yet another embodiment, the amino acid substitution in said ALS I polypeptide of a plant according to the present invention is Ala190Val, i.e., alanine at a position corresponding to position 190 of SEQ ID NO: 2 is replaced by valine.

In yet another embodiment, the amino acid substitution in said ALS III polypeptide of a plant according to the present invention is Trp556Leu, i.e., tryptophan at a position corresponding to position 556 of SEQ ID NO: 4 is replaced by leucine.

Another embodiment refers to a B. napus plant or parts thereof according to the present invention, wherein an ALS I polypeptide comprising an amino acid different from alanine at a position of said ALS I polypeptide corresponding to position 190 of SEQ ID NO: 2 is at least 90% identical to SEQ ID NO: 6 and wherein an ALS III polypeptide comprising an amino acid different from tryptophan at a position of said ALS III polypeptide corresponding to position 556 of SEQ ID NO: 4 is at least 90% identical to SEQ ID NO: 8.

Yet another embodiment refers to a B. napus plant or parts thereof according to the present invention, wherein said ALS I polypeptide is identical to SEQ ID NO: 4 and wherein said ALS III polypeptide is identical to SEQ ID NO: 8.

Yet another embodiment refers to a B. napus plant or parts thereof according to the present invention, which are tolerant to one or more ALS-inhibitor herbicides belonging to the group consisting of sulfonylurea herbicides, sulfonylaminocarbonyltriazolinone herbicides, imidazolinone herbicides, triazolopyrimidine herbicides, and pyrimidinyl(thio)benzoate herbicides.

Yet another embodiment refers to a B. napus plant or parts thereof according to the present invention, which are homozygous for the non-transgenic mutation in the ALS I alleles encoding an ALS I polypeptide comprising an amino acid different from alanine at a position corresponding to position 190 of SEQ ID NO: 2, and for the non-transgenic mutation in the ALS III alleles encoding an ALS III polypeptide comprising an amino acid different from tryptophan at a position corresponding to position 556 of SEQ ID NO: 4.

Yet another embodiment refers to parts of the B. napus plant according to the present invention, wherein the parts are organs, tissues, cells or seeds.

Another aspect refers to a method of producing an ALS inhibitor herbicide tolerant Brassica napus plant or parts thereof according to the present invention which method comprises a mutation of the genome of a Brassica napus plant by mutagenic substances or radiation. In one embodiment, a mutation is caused by a mutagenic compound such as ethyl methanesulfonate (EMS). In one embodiment, said method does not comprise a prior and/or subsequent combination of breeding and subsequent selection step.

Yet another aspect refers to An ALS inhibitor herbicide tolerant Brassica napus plant or parts thereof according to the present invention produced by subjecting a Brassica napus plant to a mutagenic substance or radiation.

Yet another aspect refers to a B. napus plant designated FM202, representative seeds of which have been deposited under NCIMB accession number NCIMB 41812, or progeny thereof obtained by further breeding with said FM202 plant, wherein said progeny contains an ALS I polypeptide comprising an amino acid different from alanine at a position of said ALS I polypeptide corresponding to position 190 of SEQ ID NO: 2 and an ALS III polypeptide comprising an amino acid different from tryptophan at a position of said ALIS III polypeptide corresponding to position 556 of SEQ ID NO: 4.

Yet another aspect refers to an Essentially Derived Variety having at least an ALS I polypeptide comprising an amino acid different from alanine at a position of said ALS I polypeptide corresponding to position 190 of SEQ ID NO: 2 and an ALS III polypeptide comprising an amino acid different from tryptophan at a position of said ALS III polypeptide corresponding to position 556 of SEQ ID NO: 4.

Yet another aspect refers to a method of producing a hybrid seed, comprising crossing a parent B. napus plant according to the present invention with a second parent Brassica plant.

Yet another aspect refers to a hybrid plant produced from crossing a parent B. napus plant according to the present invention with a second parent Brassica plant and harvesting a resultant hybrid seed and growing said seed to said hybrid plant, wherein said hybrid plant having at least an ALS I polypeptide comprising an amino acid different from alanine at a position of said ALS I polypeptide corresponding to position 205 of SEQ ID NO: 10 and an ALS III polypeptide comprising an amino acid different from tryptophan at a position of said ALS III polypeptide corresponding to position 574 of SEQ ID NO: 10.

SEQUENCES

A. thaliana sequences SEQ ID NOs: 9 (nucleotide AY042819) and 10 (protein AAK68759), and wild type B. napus sequences SEQ ID NOs: 1 (ALS1 nucleotide Z11524) and 3 (ALS3 nucleotide Z11526) were taken from the ncbi-genebank (see world wide web: http://www.ncbi.nlm-.nih.gov/genbank/). SEQ ID NOs: 2 and 4 are the protein sequences encoded by SEQ ID NOs: 1 and 3, respectively.

SEQ ID No.1: Nucleic acid sequence encoding B. napus wild type ALS I gb Z11524.

SEQ ID No.2: B. napus ALS I amino acid sequence derived from SEQ ID No. 1.

SEQ ID No.3: Nucleic acid sequence encoding B. napus wild type ALS III gb Z11526.

SEQ ID No.4: B. napus ALS III amino acid sequence derived from SEQ ID No.3.

SEQ ID No.5: Nucleic acid sequence encoding B. napus ALS I protein comprising an A190V mutation.

SEQ ID No.6: B. napus A190V ALS I amino acid sequence derived from SEQ ID No.5 (position 190 of SEQ ID NO: 6 corresponds to position 205 of SEQ ID NO: 10).

SEQ ID No.7: Nucleic acid sequence encoding B. napus ALS III protein comprising an W556L mutation.

SEQ ID No.8: B. napus W556L ALS III amino acid sequence derived from SEQ ID No.7 (position 556 of SEQ ID NO: 8 corresponds to position 574 of SEQ ID NO: 10).

SEQ ID No.9: Nucleic acid sequence encoding A. thaliana ALS gene.

SEQ ID No.10: *A. thaliana* amino acid sequence derived from SEQ ID No.9.

FIGURES

FIGS. 1A; 1B; 1C; 1D; 1E; 1F; and 1G: Alignment of nucleotide sequences SEQ ID NO: 9, 5, 1, 3, 7.

FIGS. 2A; 2B; and 2C: Alignment of protein sequences SEQ ID NO: 10, 2, 6, 4, 8.

DETAILED DESCRIPTION

General Definitions

It must be noted that as used herein, the terms "a", "an", and "the", include singular and plural references unless the context clearly indicates otherwise, i.e., such terms may refer to "one", "one or more" or "at least one". Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Plant

When used herein the term "*Brassica napus*" is abbreviated as "*B. napus*". Furthermore, the term "oilseed rape" is used herein. Said three terms are interchangeably used and should be understood to fully comprise the cultivated forms of *B. napus*, e.g., as defined in Tang et al, Plant Breeding, Volume 116, issue 5, pages 471-474, October 1997 and Jesske et al., Tagung der Vereinigung der Pflanzenzüchter and Saatgutkaufleute Österreichs, 2009, 171-172, ISBN: 978-3-902559-37-1). Similarly, for example, the term "*Arabidopsis thaliana*" is abbreviated as "*A. thaliana*". Both terms are interchangeably used herein.

The term "wild-type" as used herein refers to a plant, a nucleic acid molecule or protein that can be found in nature as distinct from being artificially produced or mutated by man. Thus, in one embodiment, a "wild type" *B. napus* plant does not produce or comprise ALS proteins with an amino acid different from alanine205 (A205) or trypthophane574 (W574 (the numbers behind the amino acids indicate the positions corresponding to these positions of SEQ ID NO: 10).

In one embodiment, a "wild-type" *B. napus* plant refers to a *B. napus* plant having at least one AHAS nucleic acid sequence of SEQ ID NO: 1 and at least one AHAS nucleic acid sequence of SEQ ID NO: 3. The use of the term "wild-type" is not intended to necessarily imply that a plant, plant tissue, plant cell, or other host cell lacks recombinant DNA in its genome, and/or does not possess herbicide resistant characteristics that are different from those disclosed herein. However, a wild type plant does not comprise an ALS I gene carrying a point mutation in the Ala190 codon (in relation to the *B. napus* ALS wild type amino acid sequence shown in SEQ ID NO: 2; this equals position 205 of the referenced *Arabidopsis thaliana* sequence as shown in SEQ ID NO: 10) yielding in an amino acid different from Ala, and an ALS III gene carrying a point mutation in the TrpSS6 codon (in relation to the *B. napus* ALS amino acid wild type sequence shown in SEQ ID NO: 4; this equals position 574 of the referenced *A. thaliana* sequence as shown in SEQ ID NO: 10) yielding in an amino acid different from Trp.

Due to the fact that the *B. napus* plants of the present invention which are herbicide resistant were generated by "random evolution", i.e., methods preferably leading to fertile *B. napus* plants having two point mutation as described herein in more detail without exogenous genetic manipulation, they are non-transgenic as far as the ALS gene in its endogenous gene locus is concerned.

Moreover, the plants of the present invention and their offspring are fertile and thus useful for breeding purposes in order to generate *B. napus* varieties conferring agronomically useful levels of tolerance to ALS inhibitor herbicides, thus allowing innovative weed control measures in *B. napus* growing areas.

The term "*Brassica* plant" as used herein refers to the genus of plants in the mustard family (Brassicaceae). The members of the genus may be collectively known either as cabbages, or as mustards. The genus "*Brassica*" encompasses. e.g., *B. carinata, B. elongata, B. fruticulosa, B. juncea, B. napus, B. narinosa, B. nigra, B. oleracea, B. perviridis, B. rapa, B. rupestris, B. septiceps,* and *B. tournefortii*. The skilled person will understand that the term not only encompasses *B. napus* but also other hybrids which have at least one parent plant of the genus "*Brassica*".

As used herein unless clearly indicated otherwise, the term "plant" intended to mean a plant at any developmental stage. Moreover, the term also encompasses "parts of a plant" in one embodiment, the term "plant" encompasses a plant as described herein and, in another embodiment, also a progeny of a plant according to the present invention.

Parts of (a) plant(s) may be attached to or separate from a whole intact plant. Such parts of a plant include, but are not limited to, organs, tissues, cells of a plant, and seeds.

In one embodiment, a *B. napus* plant of the invention comprises an ALS I protein wherein Ala at a position corresponding to position 190 of SEQ ID NO: 2 is substituted by Val and an ALS III protein wherein Trp at a position corresponding to position 556 of SEQ ID NO: 4 is substituted by Leu.

In one embodiment, a *B. napus* plant of the invention comprises an ALS I gene of SEQ ID NO: 5 and an ALS III gene of SEQ ID NO: 7.

In one embodiment, a plant in accordance with the present invention is obtainable from or derivable from or can be obtained from or derived from seeds deposited with the NCIMB, Ferguson Building, Craibstone Estate, Bucksburn, Aberdeen, AB 21 9YA UK, under the Budapest Treaty under Number NCIMB 41812 (accepted for deposit Feb. 23, 2011). In one embodiment, said plant obtainable from or derivable from or can be obtained from or derived from seeds deposited with the NCIMB under Number 41812 is a plant directly grown or regenerated from one of said deposited seeds or a plant comprising both mutant alleles described herein, i.e., an ALS I allele decoding for an ALS I protein having a mutation at a position corresponding to position 190 of SEQ ID NO:2 as described herein and an ALS III allele decoding for an ALS III protein having a mutation at a position corresponding to position 556 of SEQ ID NO: 4 as described herein. In one embodiment, such a plant obtainable from or derivable from or can be obtained from or derived from seeds deposited with the NCIMB under Number 41812 encompasses also a first, second, third, fourth or higher generation progeny of a plant directly grown or regenerated from said deposited seed or a first, second, third, fourth or higher generation progeny of a plant having at least one ALS I allele decoding for an ALS I protein having a mutation at a position corresponding to position 190 of SEQ ID NO:2 as described herein and at least one ALS III allele decoding for an ALS III protein having a mutation at a position corresponding to position 556 of SEQ ID NO: 4 as described herein. In one embodiment, such a plant is homozygous regarding its ALS I and ALS III alleles.

Moreover, also plant cells are obtainable from or are derivable from or are obtained from or are derived from said deposited seeds; or plant cells are obtainable from or are derivable from or are obtained from or are derived from plants which were grown from said deposited seeds.

Accordingly, one embodiment of the present invention is also directed to reference seeds comprising both mutant alleles described herein having been deposited under Number NCIMB 41812.

One embodiment of the present invention refers to progeny of an ALS inhibitor herbicide tolerant *B. napus* plant or parts thereof comprising an ALS I polypeptide comprising an amino acid different from alanine at a position of said ALS I polypeptide corresponding to position 190 of SEQ ID NO: 2 and an ALS III polypeptide comprising an amino acid different from tryptophan at a position of said ALS III polypeptide corresponding to position 556 of SEQ ID NO: 4.

"Progeny" as used herein refers to plants derived from an ALS inhibitor herbicide tolerant *Brassica napus* plant or parts thereof comprising an ALS I polypeptide comprising an amino acid different from alanine at a position of said ALS I polypeptide corresponding to position 190 of SEQ ID NO: 2 and an ALS III polypeptide comprising an amino acid different from tryptophan at a position of said ALS III polypeptide corresponding to position 556 of SEQ ID NO: 4, e.g., a plant obtainable from or derivable from or obtained from or derived from seeds deposited with the NCIMB, Ferguson Building, Craibstone Estate, Bucksburn, Aberdeen, AB 21 9YA UK, under the Budapest Treaty under Number NCIMB 41812 (accepted for deposit Feb. 23, 2011). Progeny may be derived by regeneration of cell or tissue culture or parts of a plant in accordance with the present invention or selfing of a plant in accordance with the present invention or by growing seeds of a plant in accordance with the present invention. In further embodiments, progeny may also encompass plants derived from crossing of at least a plant in accordance with the present invention with another *B. napus* or *Brassica* plant, backcrossing, inserting of a locus into a plant or further mutation(s). In one embodiment, a progeny is, e.g., a first generation plant such as a hybrid plant (F1) of a crossing of a plant according to the present invention with another *B. napus* or *Brassica* plant, or a progeny is regenerated from a plant part of a plant according to the present invention or is the result of self pollination. In another embodiment, a progeny is, e.g., a first, second, third, fourth, fifth, or sixth or higher generation plant derived from, derivable from, obtained from or obtainable from a *B. napus* plant in accordance with the present invention.

An "Essentially Derived Variety" (EDV) shall be deemed to be essentially derived from another variety, "the initial variety", under the following circumstances and in the case that the Initial Variety is the original mutant "FM202": (i) it is predominantly derived from the initial variety, or from a variety that is itself predominantly derived from the initial variety, while retaining the expression of the essential characteristics that result from the genotype or combination of genotypes of the initial variety, comprising an ALS I polypeptide comprising an amino acid different from alanine at a position of said ALS I polypeptide corresponding to position 205 of SEQ ID NO: 10 and an ALS III polypeptide comprising an amino acid different from tryptophan at a position of said ALS III polypeptide corresponding to position 574 of SEQ ID NO: 10; (ii) it is clearly distinguishable from the initial variety (e.g., by its phenotype or genotype); and (iii) except for the differences which result from the act of derivation, it conforms to the initial variety in the expression of the essential characteristics that result from the genotype or combination of genotypes of the initial variety. Thus, an EDV may be obtained for example by the selection of a natural or induced mutant, or of a somaclonal variant, the selection of a variant individual from plants of the initial variety, backcrossing, or transformation by genetic engineering.

"Plant line" is for example a breeding line which can be used to develop one or more varieties. One embodiment of the present invention refers to a *B. napus* plant line comprising an ALS I polypeptide comprising an amino acid different from alanine at a position of said ALS I polypeptide corresponding to position 190 of SEQ ID NO: 2 and an ALS III polypeptide comprising an amino acid different from tryptophan at a position of said. ALS III polypeptide corresponding to position 556 of SEQ ID NO: 4.

A "variety" is used herein in conformity with the UPOV convention and refers to a plant grouping within a single botanical taxon of the lowest known rank, which grouping can be defined by the expression of the characteristics resulting from a given genotype or combination of genotypes, can be distinguished from any other plant grouping by the expression of at least one of the said characteristics and is considered as a unit with regard to its suitability for being propagated unchanged (stable).

"Hybrid" refers to the seeds harvested from crossing one plant line or variety with another plant line or variety.

"$F_1$ Hybrid" refers to the first generation progeny of the cross of two genetically divergent plants. In one embodiment, such a $F_1$ Hybrid is homozygous in the essential feature, i.e., said $F_1$ Hybrid comprising ALS I alleles encoding an ALS I polypeptide comprising an amino acid different from alanine at a position of said ALS I polypeptide corresponding to position 190 of SEQ ID NO: 2 and comprising ALS III alleles encoding an ALS III polypeptide comprising an amino acid different from tryptophan at a position of said ALS III polypeptide corresponding to position 556 of SEQ ID NO: 4, and may otherwise be heterozygous.

"Crossing" refers to the mating of two parent plants.

"Backcrossing" refers to a process in which a breeder repeatedly crosses hybrid progeny, for example a first generation hybrid ($F_1$), back to one of the parents of the hybrid progeny. Backcrossing can be used to introduce one or more single locus conversions from one genetic background into another.

"Cross-pollination" refers to fertilization by the union of two gametes from different plants.

"Regeneration" refers to the development of a plant from tissue culture.

"Selfing" refers to self-pollination of a plant, i.e., the transfer of pollen from the anther to the stigma of the same plant.

Single Locus Converted (Conversion) Plant: Plants which are developed by a plant breeding technique called backcrossing, wherein essentially all of the desired morphological and physiological characteristics of a oilseed rape variety are recovered in addition to the characteristics of the single locus transferred into the variety via the backcrossing technique and/or by genetic transformation.

Plants of the present invention can be identified using any genotypic analysis method. Genotypic evaluation of the plants includes using techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), Allele-specific PCR (AS-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as "Microsatellites". Additional compositions and methods for analyzing the genotype of the plants provided herein include those methods disclosed in U.S. Publication No. 2004/0171027, U.S. Publication No. 2005/02080506, and U.S. Publication No. 2005/0283858.

Sequences/Position

The term "sequence" when used herein relates to nucleotide sequence(s), polynucleotide(s), nucleic acid sequence(s), nucleic acid(s), nucleic acid molecule, peptides, polypeptides and proteins, depending on the context in which the term "sequence" is used.

Generally, the skilled person knows, because of his common general knowledge and the context when the terms ALS, ALSL, AHAS or AHASL are used herein as to whether the nucleotide sequence or nucleic acid, or the amino acid sequence or polypeptide, respectively, is meant.

The term "position" when used in accordance with the present invention means the position of either an amino acid within an amino acid sequence depicted herein or the position of a nucleotide within a nucleotide sequence depicted herein. The term "corresponding" as used herein also includes that a position is not only determined by the number of the preceding nucleotides/amino acids.

The position of a given nucleotide in accordance with the present invention which may be substituted may vary due to deletions or additional nucleotides elsewhere in the ALS 5'-untranslated region (UTR) including the promoter and/or any other regulatory sequences or gene (including exons and introns). Similarly, the position of a given amino acid in accordance with the present invention which may be substituted may vary due to deletion or addition of amino acids elsewhere in the ALS polypeptide.

Thus, under a "corresponding position" or "a position corresponding to position" in accordance with the present invention it is to be understood that nucleotides/amino acids may differ in the indicated number but may still have similar neighbouring nucleotides/amino acids. Said nucleotides/ amino acids which may be exchanged, deleted or added are also comprised by the term "corresponding position".

In order to determine whether a nucleotide residue or amino acid residue in a given ALS nucleotide/amino acid sequence corresponds to a certain position in the nucleotide sequence of SEQ ID NO: 1, 3 or 9, respectively, or their corresponding amino acid sequences of SEQ ID NO: 2, 4 or 10, respectively, the skilled person can use means and methods well-known in the art, e.g., alignments, either manually or by using computer programs such as BLAST (Altschul et al. (1990), Journal of Molecular Biology, 215, 403-410), which stands for Basic Local Alignment Search Tool or ClustalW (Thompson et al. (1994), Nucleic Acid Res., 22, 4673-4680) or any other suitable program which is suitable to generate sequence alignments.

SEQ ID NO: 1 is the nucleotide sequence encoding *B. napus* wild type ALS I, whereas SEQ ID NO: 2 is the *B. napus* amino acid sequence derived from SEQ ID NO: 1. Accordingly, the codon at position 568-570 of the nucleotide sequence of SEQ ID NO: 1 encodes the amino acid at position 190 of SEQ ID NO: 2 (this position, again, corresponds to position 205 of SEQ ID NO: 10). In other words, the amino acid alanine ("Ala" (three letter code) or "A" (one letter code)) of SEQ ID NO: 2 is encoded by the codon at positions 568-570 of the nucleotide sequence of SEQ ID NO: 1.

SEQ ID NO: 3 is the nucleotide sequence encoding *B. napus* wild type ALS III, whereas SEQ ID NO: 4 is the *B. napus* amino acid sequence derived from SEQ ID NO: 3. Accordingly, the codon at position 1666-1668 of the nucleotide sequence of SEQ ID NO: 3 encodes the amino acid at position 556 of SEQ ID NO: 4 (this position, again, corresponds to position 574 of SEQ ID NO: 10). In other words, the amino acid tryptophan ("Trp" (three letter code) or "W" (one letter code)) of SEQ ID NO: 4 is encoded by the codon at positions 1666-1668 of the nucleotide sequence of SEQ ID NO: 3.

In the alternative to determine whether a nucleotide residue or amino acid residue in a given ALS nucleotide/ amino acid sequence corresponds to a certain position in the nucleotide sequence of SEQ ID NO: 1, 3, 5 or 7, respectively, the nucleotide sequence encoding *A. thaliana* wild type ALS shown in SEQ ID NO: 9 can be used. SEQ ID NO: 10 is the *A. thaliana* amino acid sequence derived from SEQ ID NO: 9.

The codons at position 613-615 and 1720-1722, respectively, of the nucleotide sequence of SEQ ID NO: 9 encodes the amino acid at position 205 and 574 of SEQ ID NO: 10, whereby position 205 of SEQ ID NO: 10 corresponds to position 190 of SEQ ID NOs: 2 and 6, and position 574 of SEQ ID NO: 10 corresponds to position 556 of SEQ ID NOs: 4 and 8.

If the *A. thaliana* wild type ALS nucleotide sequence shown in SEQ ID NO: 9 is used as reference sequence (as it is done in most of the relevant literature and, therefore, is used to enable an easier comparison to such known sequences), the codon encoding an amino acid different from alanine at position 190 of SEQ ID NO: 2 is at a position 568-570 of SEQ ID NO: 1 which corresponds to position 613-615 of SEQ ID NO: 9 and the codon encoding an amino acid different from tryptophan at a position 556 of SEQ ID NO: 4 is at a position 1666-1668 of SEQ ID NO: 3 which corresponds to position 1720-1722 of SEQ ID NO: 9.

However, SEQ ID NO: 1 is preferred as the reference nucleotide sequence for mutated ALS I protein encoding sequences such as SEQ ID NO: 5, and SEQ ID NO: 2 is preferred as the reference amino acid sequence for mutated sequences such as SEQ ID NO: 6 in all of the subsequent disclosures.

Similarly, SEQ ID NO: 3 is preferred as the reference nucleotide sequence for mutated ALS III protein encoding sequences such as SEQ ID NO: 7 and SEQ ID NO: 4 is preferred as the reference amino acid sequence for mutated sequences such as SEQ ID NO: 8 in all of the subsequent disclosures.

Thus, in any event, the equivalent position can still be determined through alignment with a reference sequence, such as SEQ ID NO: 1 or 5 (nucleotide sequence) or SEQ ID NO: 2 or 6 (amino acid sequence). Alignments of the various sequences listed above are given in figures I and II.

In view of the difference between the B. napus wild-type ALS genes (ALS I and III gene) and the mutated ALS genes comprised by a B. napus plant of the present invention or progeny thereof, the ALS genes (or polynucleotides or nucleotide sequences) comprised by a B. napus plant of the present invention or progeny thereof may also be regarded as a "mutant ALS gene", "mutant ALS allele", "mutant ALS polynucleotide" or the like. Thus, throughout the specification, the terms "mutant allele", "mutant ALS allele", "mutant ALS gene" or "mutant ALS polynucleotide" are used interchangeably.

Unless indicated otherwise herein, these terms refer to a nucleotide sequence encoding an ALS I protein that comprises a codon at a position which corresponds to position 568-570 of SEQ ID NO: 1 and said codon encodes an amino acid different from alanine; and to a second nucleotide sequence encoding for an ALS III protein that comprises a codon at a position which corresponds to position 1666-1668 of SEQ ID NO: 3 and said codon of said second nucleotide sequence encodes an amino acid different from tryptophan.

The terms "nucleotide sequence(s)", "polynucleotide(s)", "nucleic acid sequence(s)", "nucleic acid(s)", "nucleic acid molecule" are used interchangeably herein and refer to nucleotides, either ribonucleotides or deoxyribonucleotides or a combination of both, in a polymeric unbranched form of any length. Nucleic acid sequences include DNA, cDNA, genomic DNA, RNA, synthetic forms and mixed polymers, both sense and antisense strands, or may contain non-natural or derivatized nucleotide bases, as will be readily appreciated by those skilled in the art.

Homology/Identity

In order to determine whether a nucleic acid sequence has a certain degree of identity to the nucleotide sequences of the present invention, the skilled person can use means and methods well-known in the art, e.g., alignments, either manually or by using computer programs such as those mentioned further down below in connection with the definition of the term "hybridization" and degrees of homology.

For the purpose of this invention, the "sequence identity" or "sequence homology" (the terms are used interchangeably herein) of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. http://www.ebi.ac.uk/emboss/align/index.html) using default settings gap opening penalty=10 (for nucleotides)/10 (for proteins) and gap extension penalty=0.5 (for nucleotides)/0.5 (for proteins)). For nucleotides the default scoring matrix used is EDNAFULL and for proteins the default scoring matrix is EBLOSUM62.

The term B. napus "ALS" or "AHAS" gene also includes B. napus nucleotide sequences which are at least 60, 70, 80, 90, 95, 97, 98, or 99% identical to the B. napus ALS nucleotide sequence of SEQ ID NO: 1 or 3, wherein these 60, 70, 80, 90, 95, 97, 98, or 99% identical nucleotide sequences comprise at a position corresponding to position 568-570 of the nucleotide sequence of SEQ ID NO: 1 a codon encoding an amino acid different from Ala (at position 190 of SEQ ID NO: 2) or at a position corresponding to position 1666-1668 of the nucleotide sequence of SEQ ID NO: 3 a codon encoding an amino acid different from Trp (at position 556 of SEQ ID NO: 4).

Likewise, these at least 60, 70, 80, 90, 95, 97, 98, or 99% identical nucleotide sequences encode an ALS polypeptide comprising at a position corresponding to position 190 of SEQ ID NO: 2 an amino acid different from Ala, or at a position corresponding to position 556 of SEQ ID NO: 4 an amino acid different from Trp. Of course, these nucleotide sequences encode for ALS proteins which retains the activity as described herein, more preferably the thus-encoded ALS polypeptide is tolerant to one or more ALS inhibitor herbicides as described herein. Said term also includes allelic variants and homologs encoding an ALS polypeptide which is preferably tolerant to one or more ALS inhibitor herbicides as described herein.

When used herein, the term "polypeptide" or "protein" (both terms are used interchangeably herein) means a peptide, a protein, or a polypeptide which encompasses amino acid chains of a given length, wherein the amino acid residues are linked by covalent peptide bonds. However, peptidomimetics of such proteins/polypeptides wherein amino acid(s) and/or peptide bond(s) have been replaced by functional analogs are also encompassed by the invention as well as other than the 20 gene-encoded amino acids, such as selenocysteine. Peptides, oligopeptides and proteins may be termed polypeptides. The term polypeptide also refers to, and does not exclude, modifications of the polypeptide, e.g., glycosylation, acetylation, phosphorylation and the like. Such modifications are well described in basic texts and in more detailed monographs, as well as in the research literature. The polypeptide (or protein) that are preferably meant herein are the mutated B. napus ALS I and III polypeptidea (or ALS I and III proteins) of SEQ ID NO: 6 and 8, respectively.

The term B. napus "ALS" or "AHAS" polypeptide also includes amino acid sequences which are at least 90, 95, 97, 98, or 99% identical to the ALS amino acid sequence of SEQ ID NO: 2 or 4, wherein these at least 90, 95, 97, 98, or 99% identical amino acid sequences comprising at a position corresponding to position 190 of SEQ ID NO: 2 an amino acid different from alanine and at a position corresponding to position 556 of SEQ ID NO: 4 an amino acid different from tryptophan. Said X % identical amino acid sequences retain the activity of ALS as described herein, more preferably the ALS polypeptide is tolerant to ALS inhibitor herbicides as described herein. However, such "ALS" or "AHAS" polypeptides still show ALS activity of at least 20%, 30%, 40%, 50%, 60%, 70%, 80%, 90% compared to ALS activity of an protein having the SEQ ID NO: 2 (when referring to an ALS protein) or 4 (when referring to an ALS III protein).

The same techniques, e.g., BLAST, as described above for the alignment of nucleic acid sequences can be used for alignments of protein sequences as well. For Example, a BLAST search can be performed from those skilled in the art using ExPASy (see world wide net: http://expasy.org/tools/).

Isolated/Purified

An "isolated" nucleic acid sequence (or DNA) is used herein to refer to a nucleic acid sequence (or DNA) that is no longer in its natural environment, for example in an in vitro or in a recombinant bacterial or plant host cell. In some embodiments, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated nucleic acid molecule encoding a pesticidal protein can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A pesticidal protein that is substantially free of cellular material includes preparations of protein having less than about 30%, 20%, 10%, or 5% (by dry weight) of non-pesticidal protein (also referred to herein as a "contaminating protein").

Amino Acid Substitution

Amino acid substitutions encompass amino acid alterations in which an amino acid is replaced with a different naturally-occurring amino acid residue. Such substitutions may be classified as "conservative", in which an amino acid residue contained in the wild-type ALS protein is replaced with another naturally-occurring amino acid of similar character, for example Ala↔Val, Trp↔Leu, Gly↔Asp, Gly↔Ala, Val↔Ile↔Leu, Asp↔Glu, Lys↔Arg, Asn↔Gln or Phe↔Trp↔Tyr. Substitutions encompassed by the present invention may also be "non-conservative", in which an amino acid residue which is present in the wild-type ALS protein is substituted with an amino acid with different properties, such as a naturally-occurring amino acid from a different group. In one embodiment, a plant comprises non-transgenic mutations of its endogenous acetolactate synthase (ALS) genes, wherein an ALS I gene encodes an ALS I polypeptide comprising an amino acid different from alanine at a position corresponding to position 190 of SEQ ID NO: 2 and wherein an ALS III gene encodes an ALS III polypeptide comprising an amino acid different from tryptophan at a position corresponding to position 559 of SEQ ID NO: 4. In one embodiment, the mutations lead to a substitution of Ala190Val and Trp556Leu. In another embodiment, altered gen sequences of ALS I gene sequence SEQ ID NO: 1 and/or ALS III gene sequence SEQ ID NO: 3 may contain at least one further mutation.

"Similar amino acids", as used herein, refers to amino acids that have similar amino acid side chains, i.e. amino acids that have polar, non-polar or practically neutral side chains. "Non-similar amino acids", as used herein, refers to amino acids that have different amino acid side chains, for example an amino acid with a polar side chain is non-similar to an amino acid with a non-polar side chain. Polar side chains usually tend to be present on the surface of a protein where they can interact with the aqueous environment found in cells ("hydrophilic" amino acids). On the other hand, "non-polar" amino acids tend to reside within the center of the protein where they can interact with similar non-polar neighbours ("hydrophobic" amino acids"). Examples of amino acids that have polar side chains are arginine, asparagine, aspartate, cysteine, glutamine, glutamate, histidine, lysine, serine, and threonine (all hydrophilic, except for cysteine which is hydrophobic). Examples of amino acids that have non-polar side chains are alanine, glycine, isoleucine, leucine, methionine, phenylalanine, proline, and tryptophan (all hydrophobic, except for glycine which is neutral).

An "amino acid different from alanine" ("Ala" or "A") includes any naturally-occurring amino acid different from Ala. These naturally-occurring amino acids include neutral-nonpolar amino acids tryptophan (W), valine (V), methionine (M), isoleucine (I), leucine (L), proline (P), phenylalanine (F), basic amino acids arginine (R), lysine (K), histidine polar/neutral amino acids aspartate (D), cysteine (C), glutamate (E), glycine (G), serine (S), threonine (T), tyrosine (Y) and acidic amino acids glutamine (Q) and asparagine (N).

In one embodiment, the "amino acid different from alanine" is an amino acid with physico-chemical properties different from alanine, i.e. belonging to any of the amino acids showing neutral-polar, acidic, or basic properties. In another embodiment, the amino acid different from alanine is another neutral-nonpolar amino acid. In one embodiment, such a neutral-nonpolar amino acid is valine, leucine or isoleucine. In another embodiment, said neutral-nonpolar amino acid is valine. In one embodiment, the amino acid different from alanine is glycine, isoleucine, leucine, methionine, phenylalanine, proline, valine, or arginine. In another embodiment, said amino acid different from alanine is glycine, isoleucine, leucine, methionine, phenylalanine, proline or valine. In yet another embodiment, said amino acid different from alanine is valine, glycine, isoleucine or leucine. In even another embodiment, said amino acid different from alanine is valine, glycine and leucine. In one embodiment, said amino acid is valine.

An "amino acid different from tryptophan" ("Trp" or "W") includes any naturally-occurring amino acid different from Trp. These naturally-occurring amino acids include alanine (A), arginine (R), asparagine (N), aspartate (D), cysteine (C), glutamine (Q), glutamate (E), glycine (G), histidine (H), isoleucine (I), leucine (L), lysine (K), methionine (M), phenylalanine (F), proline (P), serine (S), threonine (T), tyrosine (Y) or valine (V).

In one embodiment, the amino acid different from tryptophan is an amino acid with physico-chemical properties different from alanine. i.e. belonging to any of the amino acids showing neutral-polar, acidic, or basic properties. In another embodiment, the amino acid different from alanine is another neutral-nonpolar amino acid. In one embodiment, the amino acid different from Trp is alanine, glycine, isoleucine, leucine, methionine, phenylalanine, proline, valine, and arginine. In another embodiment, said amino acid different from tryptophan is alanine, glycine, isoleucine, leucine, methionine, phenylalanine, proline or valine. In yet another embodiment, said amino acid different from tryptophan is alanine, glycine, isoleucine, leucine or valine. In even another embodiment, said amino acid different from tryptophan is glycine and leucine. In one embodiment, said amino acid different from tryptophan is leucine.

Genes/Alleles

Unless indicated otherwise, the terms "wild-type allele," "wild-type ALS allele", "wild-type ALS gene" or "wild-type ALS polynucleotide" refer to a nucleotide sequence that encodes an ALS protein that lacks the Ala190 substitution, e.g., in relation to SEQ ID NO: 2; and to a nucleotide sequence that encodes an ALS III protein that lacks the Trp556 substitution, e.g., in relation to SEQ NO: 4.

Such a "wild-type allele", "wild-type ALS allele", "wild-type ALS gene" or "wild-type ALS polynucleotide" may, or may not, comprise mutations, other than the mutation mentioned above. However, SEQ ID NO: 1 and SEQ ID NO: 3 are in any case "wild-type alleles" which can be used as a reference.

The term "gene" when used herein refers to a polymeric form of nucleotides of any length, either ribonucleotides or desoxyribonucleotides. The term includes double- and single-stranded DNA and RNA. It also includes known types of modifications, for example, methylation, "caps", substitutions of one or more of the naturally occurring nucleotides with an analog. Preferably, a gene comprises a coding sequence encoding the herein defined polypeptide. A "coding sequence" is a nucleotide sequence which is transcribed into mRNA and/or translated into a polypeptide when placed or being under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleic acid sequences or genomic DNA, while introns may be present as well under certain circumstances.

In essence, the difference between a wild-type B. napus plant, and a B. napus plant of the present invention is that at least an ALS I gene comprises a codon—corresponding to position 568-570 of SEQ ID NO: 1—encodes an amino acid different from Ala; and that at least an ALS III gene comprises a codon—corresponding to position 1666-1668 of the SEQ ID NO: 3—encodes an amino acid different from Trp.

In one embodiment, these codons encode an amino acid as specified herein elsewhere. However, as mentioned above, further differences such as additional mutations may be present between wild-type and the mutant ALS allele as specified herein. Yet, these further differences are not relevant as long as the difference explained before is present.

In one embodiment, a plant according to the present invention comprises an ALS I gene which encodes an ALS I protein comprising an amino acid different from Ala at a position 190 when comparing said ALS I protein with the wild type amino acid sequence SEQ ID NO: 2; and comprises an ALS III gene which encodes an ALS III protein comprising an amino acid different from Trp at a position 556 when comparing said ALS III protein with the wild type amino acid sequence SEQ ID NO: 4.

In one embodiment, a plant according to the present invention comprises an ALS I gene encoding an ALS I protein wherein the amino acid different from Ala is Val; and an ALS III gene encoding an ALS III protein wherein the amino acid different from Trp is Leu. The skilled person will understand that such mutated ALS I and ALS III genes may comprise further mutations such as one, two or three further mutations.

Consequently, the Ala205 and Trp574 substitutions (when the A. thaliana ALS amino acid sequence of SEQ ID NO: 10 is used as reference) are a result of an alteration of codons at a position corresponding to position 613-615 and 1720-1722 of the nucleotide sequence shown in SEQ ID NO: 9.

In one embodiment, the substitution at position 205 (when the A. thaliana ALS amino acid sequence of SEQ ID NO: 10 is used as reference) is an A→V substitution, wherein "V" is encoded by any of the codons "GTT", "GTC", "GTA" or "GTG" and the substitution at position 574 (when the A. thaliana ALS amino acid sequence of SEQ ID NO: 10 is used as reference) is a W→L substitution, wherein "L" is encoded by any of the codons "CTT", "CTC", "CTA", "CTG", "TTA", "TTG".

Hence, in one embodiment, the present invention provides a B. napus plant comprising in the nucleotide sequence of an ALS I gene in its endogenous gene locus, at least a codon encoding an amino acid different from Ala, preferably Val, at a position corresponding to position 613-615 of the A. thaliana ALS nucleic acid sequence of SEQ ID NO: 9 and comprising in the nucleotide sequence of an ALS III gene in its endogenous gene locus, at least a codon encoding an amino acid different from Trp, preferably Leu, at a position corresponding to position 1720-1722 of the A. thaliana ALS nucleic acid sequence of SEQ ID NO: 9.

ALS Activity Tolerance

For the present invention, the terms "herbicide-tolerant" and "herbicide-resistant" are used interchangeably and are intended to have an equivalent meaning and an equivalent scope. Similarly, the terms "herbicide-tolerance" and "herbicide-resistance" are used interchangeably and are intended to have an equivalent meaning and an equivalent scope.

It is preferred that the B. napus plants of the present invention are less sensitive to an ALS inhibitor, more preferably it is at least 100 times less sensitive, more preferably, 500 times, even more preferably 1000 times and most preferably less than 2000 times compared to wild type plants comprising, e.g., ALS I polypeptides of SEQ ID NO: 2 and ALS III polypeptides of SEQ ID NO: 4, i.e., wild type plants having not the substitutions of the present invention. Wild type plants wherein all ALS I alleles are alleles of SEQ ID NO: 1 and all ALS III alleles are alleles of SEQ ID NO: 3 are preferred references when comparing ALS sensitivity. Less sensitive when used herein may, vice versa, be seen as "more tolerable" or "more resistant". Similarly, "more tolerable" or "more resistant" may, vice versa, be seen as "less sensitive".

For example, the B. napus plants of the present invention and in particular the B. napus plant described in the appended Examples are/is at least 1000 times less sensitive to the ALS inhibitor herbicide foramsulfuron (a member of the ALS inhibitor subclass "sulfonylurea herbicides") compared to the wild type enzyme.

An "herbicide-tolerant" or "herbicide-resistant" plant refers to a plant that is tolerant or resistant to at least one AHAS-inhibiting herbicide at a level that would normally kill, or inhibit the growth of a normal or wild-type plant lacking a mutated AHAS nucleic acid molecule. By "herbicide-resistant AHAS nucleic acid molecule" is intended a nucleic acid molecule comprising one or more mutations that results in one or more amino acid substitutions relative to the non-mutated AHAS protein, where the mutations result in the expression of an herbicide-resistant AHAS protein. By "herbicide-tolerant AHAS protein" or "herbicide-resistant AHAS protein", it is intended that such an AHAS protein displays higher AHAS activity, relative to the AHAS activity of a wild-type AHAS protein, when in the presence of at least one herbicide that is known to interfere with AHAS activity and at a concentration or level of the herbicide that is to known to inhibit the AHAS activity of the wild-type AHAS protein. Furthermore, the AHAS activity of such an herbicide-tolerant or herbicide-resistant AHAS protein may be referred to herein as "herbicide-tolerant" or "herbicide-resistant" AHAS activity.

Preferably, the *B. napus* plants of the present invention are less sensitive to various members of ALS inhibitor herbicides, like sulfonylurea herbicides, sulfonylamino-carbonyi-triazolinone herbicides, and imidazolinone herbicides. Sulfonylurea herbicides and sulfonylaminocarbonyltriazolinone herbicides against which said plants are less sensitive are preferably selected. In a particular preferred embodiment, the *B. napus* plants of the present invention are less sensitive to the ALS inhibitor herbicide foramsulfuron (sulfonylurea herbicide) either alone or in combination with one or more further ALS inhibitor herbicides either from the subclass of the sulfonyurea-herbicides or any other sub-class of the ALS inhibitor herbicides, e.g. a compound of formula (I):

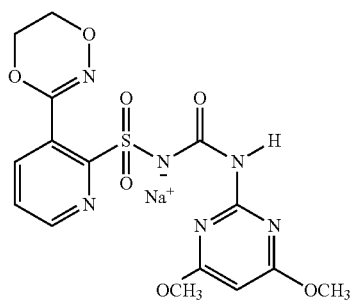

(I)

Hence, the *B. napus* plants of the present invention which are preferably less sensitive to an ALS inhibitor herbicide can likewise also be characterized to be "more tolerant" to an ALS inhibitor" (i.e. an ALS inhibitor tolerant plant).

Thus, an "ALS inhibitor tolerant" plant refers to plant, preferably a *B. napus* plant according to the present invention or any of its progenies that is more tolerant to at least one ALS inhibitor herbicide at a level that would normally inhibit the growth of a normal or wild-type plant, preferably the ALS inhibitor herbicide controls a normal or wild-type plant. Said normal or wild-type plant does not comprise in the nucleotide sequence of any allele of the endogenous ALS I gene, a codon encoding an amino acid different from Ala at a position corresponding to position 568-570 of SEQ ID NO: 1 and does not comprise in the nucleotide sequence of any allele of the endogenous ALS III gene, a codon encoding an amino acid different from Trp at a position corresponding to position 1666-1668 of SEQ ID NO: 3.

Said nucleotide sequences may generally also be characterized to be "ALS inhibitor herbicide tolerant" nucleotide sequences. By "ALS inhibitor herbicide tolerant nucleotide sequence" is intended a nucleic acid molecule comprising nucleotide sequences encoding for a ALS I protein having at least an amino acid different from Ala at a position corresponding to position 190 of SEQ ID NO: 2 and/or c nucleotide sequences encoding for a ALS III protein having at least an amino acid different from Trp at a position corresponding to position 556 of SEQ ID NO: 4, wherein said at least one mutations results in the expression of a less sensitive to an ALS inhibitor herbicide ALS protein.

By "herbicide-tolerant ALS protein", it is intended that such an ALS protein displays higher ALS activity, relative to the ALS activity of a wild-type ALS protein, in the presence of at least one ALS inhibitor herbicide that is known to interfere with ALS activity and at a concentration or level of said herbicide that is known to inhibit the ALS activity of the wild-type ALS protein.

Similarly, the terms "ALS-inhibitor herbicide(s)" or simply "ALS-inhibitor(s)" are used interchangeably. As used herein, an "ALS-inhibitor herbicide" or an "ALS inhibitor" is not meant to be limited to single herbicide that interferes with the activity of the ALS enzyme. Thus, unless otherwise stated or evident from the context, an "ALS-inhibitor herbicide" or an "ALS inhibitor" can be a one herbicide or a mixture of two, three, four, or more herbicides known in the art, preferably as specified herein, each of which interferes with the activity of the ALS enzyme.

"Herbicide resistance" or "herbicide tolerance" can, be measured as described in the present application or, e.g., it can be measured by comparison of AHAS activity obtained from cell extracts from plants containing the mutagenized AHAS sequence and from plants lacking the mutagenized AHAS sequence in the presence of an AHAS inhibitor, such as foramsulfuron or imazamox, using the methods disclosed in Singh, et al. Anal. Biochem., (1988), 171: 173-179. In one embodiment, resistant or tolerant plants demonstrate greater than 25% uninhibition using the methods disclosed in Singh et al (1988) when assayed, e.g., using 10 µM foramsulfuron or 10 µM imazamox.

The activity of specific ALS proteins such as ALS I or ALS III proteins can be measured according to the following method: The coding sequences of *B. napus* wild-type and A205-mutant ALS I or W574-mutant ALS III genes can be cloned into Novagen pET-32a(+) vectors and the vectors transformed into *Escherichia coli* AD494 according to the instructions of the manufacturer. Bacteria were grown at 37° C. in LB-medium containing 100 mg/l carbenicillin and 25 mg/l canamycin, induced with 1 mM isopropyl-β-D-thioga-lactopyranoside at an $OD_{600}$ of 0.6, cultivated for 1.6 hours at 18° C. and harvested by, e.g., centrifugation. Bacterial pellets were resuspended in 100 mM sodium phosphate buffer pH 7.0 containing 0.1 mM thiamine-pyrophosphate, 1 mM $MgCl_2$, and 1 µM FAD at a concentration of 1 gram wet weight per 25 ml of buffer and disrupted by, e.g., sonication. The crude protein extract obtained after centrifugation was used for ALS activity measurements.

ALS protein can be extracted from *B. napus* leaves or *B. napus* tissue cultures as described by Ray (Plant Physiol, 1984, 75:827-831). An ALS assays can be carried out in 96-well microtiter plates using a modification of the procedure described by Ray (1984): The reaction mixture contains 20 mM potassium phosphate buffer pH 17.0, 20 mM sodium pyruvate, 0.45 mM thiamine-pyrophosphate, 0.45 mM $MgCl_2$, 9 M FAD. ALS enzyme and various concentrations of ALS inhibitors can be mixed in a final volume of 90 µl. Assays can be initiated by adding enzyme and the assays can be terminated after 75 min incubation at 30° C. by the addition of 40 µl 0.5 M $H_2SO_4$. After 60 min at room temperature 80 µl of a solution of 1.4% α-naphtol and 0.14% creatine in 0.7 M NaOH can be added and after an additional 45 min incubation at room temperature the absorbance can be determined at 540 nm. pI50-values for inhibition of ALS can be determined as described by Ray (1984), using the XLFit Excel add-in version 4.3.1 curve fitting program of ID Business Solutions Limited.

The ALS nucleotide sequences referred to herein encoding ALS polypeptides preferably confer tolerance to one or more ALS inhibitor herbicides (or, vice versa, less sensitivity to an ALS inhibitor herbicide) as described herein. This is because of the point mutation leading to an amino acid substitution as described herein. In one embodiment, the plants of the present invention show tolerance against a compound of formula (I), e.g., plants according to the invention show essentially no injury (injury below 5%, 1% or even 0%) when 15 g a.i./ha are applied whereas injury of wild type, e.g., SR002201 is above 90%.

Tolerance

Surprisingly, it was found that the at least one point mutation in an ALS I gene and in an ALS III gene, respectively, in accordance with the present invention confers agronomically useful and stable levels of ALS inhibitor herbicide tolerance in *B. napus* plants as well as in their offsprings, particularly, if homozygocity is established. Compared to herbicide tolerant *B. napus* plants of the same genetic background in which such mutation is only heterozygously present, the herbicide tolerant *B. napus* plants which are homozygous for the non-transgenic mutation revealed a better agronomical level of ALS inhibitor herbicide tolerance.

One embodiment of the present invention refers to *B. napus* plants and parts thereof and progeny thereof which are heterozygous for the non-transgenic mutations described herein. Thus, also covered by the present invention are plants comprising at least in one allele of the ALS I gene in its endogenous gene locus a codon encoding an amino acid different from Ala, preferably Val, at a position corresponding to position 568-570 of SEQ ID NO: 1, and comprising one or more further ALS I alleles encoding independently from each other Ala at a position corresponding to position 568-570 of SEQ ID NO: 1 wherein said further allele optionally comprise independently from each other at least one, two or three further mutations; and comprising in at least one allele of the ALS III gene in its endogenous gene locus a codon encoding an amino acid different from tryptophan, preferably leucine, at a position corresponding to position 1666-1668 of SEQ ID NO: 3, and comprising one or more further ALS III allele(s) having independently from each other a codon at a position corresponding to position 1666-1668 of SEQ ID NO: 3 encoding Trp wherein said further ALS III alleles optionally comprise independently from each other at least one, two or three further mutations.

However, one embodiment of the invention refers to *B. napus* plants and parts thereof which are homozygous regarding the point mutation of ALS I genes at a position corresponding to position 190 of SEQ ID NO: 1; and the point mutation of ALS III genes at a position corresponding to position 556 of SEQ ID NO: 3 leading to amino acids different from alanine and tryptophan, respectively.

As used herein, the term "heterozygous" means a genetic condition existing when (at least) two different alleles reside at a specific locus, but are positioned individually on corresponding pairs of homologous chromosomes in the cell. In other words, (at least) two different ALS I alleles and (at least) two different ALS III alleles, respectively, reside at specific loci but are positioned individually on corresponding pairs of homologous chromosomes in the cell.

Conversely, as used herein, the term "homozygous" means a genetic condition existing when two (all) identical alleles reside at a specific locus, but are positioned individually on corresponding pairs of homologous chromosomes in the cell.

As used herein, the term "locus" (loci plural) means a specific place or places or a site on a chromosome where, e.g., a gene or genetic marker is found.

As mentioned herein, the *B. napus* plant of the present invention comprises in the nucleotide sequence of at least one ALS I gene in its endogenous gene locus a codon encoding an amino acid different from Ala at a position as specified herein and in the nucleotide sequence of at least one ALS III gene in its endogenous gene locus a codon encoding an amino acid different from Trp at a position as specified herein. By ALS genes in its "endogenous locus" it is meant that the ALS genes comprised by the *B. napus* plant of the present invention is—when compared to a wild-type *B. napus* plant—located in the same locus, i.e., the ALS genes are positioned (located) on the same chromosome in the same chromosomal context (organization) as they are positioned in a wild-type plant (i.e., without there being any human intervention so as to transfer or re-locate the ALS genes comprised by the *B. napus* plant of the present invention to another location such as to another chromosome or genomic locus (position) different from that where the ALS genes are naturally located). Accordingly, the identical genome-specific satellite markers which surround a wild-type ALS gene also surround an ALS gene comprised by the *B. napus* plant of the present invention.

"Chromosomal context (organization)" means that an ALS gene of the *B. napus* plant of the present invention is located on the same chromosome as it is in a wild-type *B. napus* plant. Accordingly, the same genes as in a wild-type *B. napus* plant are adjacent to the 5'- and 3'-end of an ALS gene comprised by the *B. napus* plant of the present invention. Hence, the same nucleotide sequences which are adjacent to the 5'- and 3'-end of the wild-type ALS gene are adjacent to the 5'- and 3'-end of an ALS gene comprised by the *B. napus* plant of the present invention. The similarity of the chromosomal context between an ALS gene comprised by the *B. napus* plant of the present invention and that of an ALS gene of a wild-type *B. napus* plant can, for example, be tested as follows:

Genome-specific satellite markers which surround a wild-type ALS gene and an ALS gene of the present invention can be used together with sequences from the *B. napus* ALS gene (preferably except for the codon at the position as specified herein which is different between the wild-type ALS gene and an ALS gene comprised by the *B. napus* plant of the present invention) for primer design and subsequent nucleic acid amplification, whereby the amplification product will be identical between a wild-type *B. napus* plant and the *B. napus* plant of the present invention. These genome-specific satellite markers can also be used for a fluorescent in situ hybridization (FISH) in order to check the location of the ALS gene (see Schmidt and Heslop-Harrison (1996), Proc. Natl. Acad. Sci. 93:8761-8765 for a FISH protocol of *B. napus*).

In view of the fact that mutated endogenous ALS I and III genes of the present invention are located at the same chromosome at the same specific location, respectively, the "staining pattern" in FISH of the chromosome on which the wild-type *B. napus* ALS I and III genes are located will be identical to the staining pattern in FISH of the chromosome on which the *B. napus* ALS I and III genes of the present invention are located.

Accordingly, the plant of the present invention is non-transgenic as regards to endogenous ALS I and III genes. Of course, foreign genes can be transferred to the plant either by genetic engineering or by conventional methods such as crossing. Said genes can be genes conferring herbicide tolerances, preferably conferring herbicide tolerances different from ALS inhibitor herbicide tolerances, genes improving yield, genes improving resistances to biological organisms, and/or genes concerning content modifications.

In a further aspect, the present invention relates to a method for the manufacture of the *B. napus* plant and the parts thereof, comprising the following steps:

(a) exposing microspore-derived embryos, microspore-derived tissues or calli from *B. napus* to about $10^{-6}$ M-$10^{-9}$ M of an ALS inhibitor herbicide, such as foramulfuron [CAS RN 173159-57-4], thiencarhazone or a compound of formula (I);
(b) selecting cell colonies which can grow in the presence of up to $3\times10^{-6}$ M of an ALS inhibitor herbicide, such as foramsulfuron, thiencarbazone or a compound of formula (I);
(c) regenerating shoots in presence of an ALS inhibitor herbicide, such as foramsulfuron, thiencarhazone or a compound of formula (I);
(d) selecting regenerated plantlets with an ALS inhibitor herbicide, such as foramsulfuron, thiencarhazone or a compound of formula (I) and/or a mixture thereof, wherein the dose of foramsulfuron is in some embodiments equivalent to 7-70 g a.i./ha, the dose of thiencarbazone is in one embodiment equivalent to 5-20 g a.i./ha, the dose of a compound of formula (I) is in one embodiment equivalent to 3-20 g a.i./ha.

In a further aspect, the regenerated plantlets obtained according to the processes (a) to (d) above, can be employed for further manufacture of *B. napus* plants by applying the following steps (e) to (m):

(e) vegetative micropropagation of individual plantlets of step (d) to rescue different positive variants by establishing a cell line (clone) of each ALS inhibitor herbicide tolerant plantlet;
(f) optionally long term storage of each established clone in the vegetative state;
(g) transfer of cloned plants of each clone into the greenhouse or transfer of cloned plants of each clone from the long term storage into the greenhouse;
(h) vernalisation and adaptation in vernalisation chambers to induce flowering;
(i) transfer of vernalised plants to growth rooms (controlled temperature and light);
(j) select best pollen shedding plants of best flowering clones for crossing with emasculated plants of an elite but ALS inhibitor herbicide sensitive line to overcome the negative impact of somaclonal variation on the generative fertility (male and female) of plantlets of step (d);
(k) backcross to elite line until fertility is restored and finally self heterozygous plants to reach the homozygous state;
(l) produce testcrosses with an ALS inhibitor herbicide-sensitive partner and selfed seed of each backcrossed line for field evaluations;
(m) applying agronomically relevant dose rates of different ALS inhibitor herbicides to select the best performing line, preferably in its homozygous state.

The plant lines obtained according to above steps (a) to (m) form the basis for the development of commercial varieties including F1 hybrids following procedures known in the breeding community supported by molecular breeding techniques (like marker assisted breeding or marker assisted selection) for speeding up the processes and to secure the correct selection of plants to either obtain the mutation in its homozygous form or in case of comprising one or more mutations at various locations of the ALS encoding endogenous gene to perform the correct selection of heterozygous plants wherein at least at one of the alleles of ALS I comprises the Ala205 mutation (when referring to SEQ ID NO: 10) according to present invention and at least one of the alleles of ALS III comprises the Trp574 mutation (when referring to SEQ ID NO: 10) according to the present invention.

Calli are obtained by means and methods commonly known in the art, e.g., Alexander Dovzhenko, PhD Thesis, Title: "Towards plastid transformation in rapeseed (*Brassica napus* L.) and sugarbeet (*Beta vulgaris* L.)", Ludwig-Maximilians-Universitat München, Germany, 2001):

*B. napus* seeds can be immersed for 60 seconds in 70% ethanol, then rinsed twice in sterile water with 0.01% detergent and then incubated for 1-4 hours in 1% NaOCl bleach. After washing with sterile $H_2O$ at 4° C., the embryos can be isolated using, e.g., forceps and scalpel.

The freshly prepared embryos can be immersed in 0.5% NaOCl for 30 min and then washed in sterile $H_2O$. After the last washing step they can be placed on hormone free MS agar medium (Murashige and Skoog (1962), Physiol. Plantarum, 15, 473-497). Those embryos which developed into sterile seedlings can be used for the initiation of regenerable *B. napus* cell cultures.

Cotyledons as well as hypocotyls can be cut into 2-5 mm long segments and then cultivated on agar (0.8%) solidified MS agar medium containing either 1 mg/l Benzylaminopurin (BAP) or 0.25 mg/l Thidiazuron (TDZ). 4 weeks later the developing shoot cultures can be transferred onto fresh MS agar medium of the same composition and then sub-cultured in monthly intervals. The cultures can be kept at 25° C. under dim light at a 12 h/12 h light/dark cycle.

After 7-10 days, subcultures the shoot cultures which were grown on the thidiazuron containing medium formed a distinct callus type, which was fast growing, soft and friable. The colour of this callus type is typically yellowish to light green. Some of these friable calli consistently produced chlorophyll containing shoot primordia from embryo-like structures. These fast growing regenerable calli can be used for the selection of ALS inhibitor herbicide tolerant *B. napus* mutants.

Wild type seeds SR002201 for microspore isolation, culture and selection experiments of mutants have been deposited with the NCIMB, Aberdeen, UK, under Number NCIMB 41813.

In a further aspect, the present invention relates to a method for producing an herbicide tolerant *B. napus* plant and parts thereof comprising (i) a non-transgenic mutation of an endogenous ALS I gene, wherein the ALS I gene encodes an ALS I polypeptide comprising an amino acid different from Ala at a position corresponding to position 190 of SEQ ID NO: 2 and (ii) an endogenous ALS III gene, wherein the ALS III gene encodes an ALS III polypeptide comprising an amino acid different from Trp at a position corresponding to position 556 of SEQ ID NO: 4 and (iii), at least one further mutation in an ALS gene comprising the following steps:

(a) producing an ALS inhibitor herbicide tolerant *B. napus* plant comprising a non-transgenic mutation of an endogenous ALS I gene, wherein the ALS I gene encodes an ALS polypeptide comprising an amino acid different from Ala at a position corresponding to position 190 of SEQ ID NO: 2 and an endogenous ALS III gene, wherein the ALS III gene encodes an ALS III polypeptide comprising an amino acid different from Trp at a position corresponding to position 556 of SEQ ID NO: 4 (parent A);

(b) crossing parent A with a *Brassica* plant (parent B), such as a *B. napus* plant, comprising one or more further mutations in an endogenous ALS gene at positions differing from amino acid position 190 of an ALS I nucleotide sequence and position 556 of an ALS III nucleic sequence;

(c) obtaining a *B. napus* progeny that is heterozygous or homozygous for the ALS I gene mutation of amino acid position 190, for the ALS III gene mutation of amino acid position 556 and to one or more of any further ALS gene mutations encoded by parent B;

(d) wherein the breeding process is controlled by
  (i) the application of marker assisted breeding and/or microsequencing techniques, and/or
  (ii) the application of agronomically relevant doses of one or more ALS inhibitor herbicides to which the generated progeny according to step (c) is tolerant.

Accordingly, it is envisaged that the present invention also relates to *B. napus* plants obtainable by the aforementioned methods of manufacture.

In a non-limiting example, *B. napus* plants of the present invention were obtained by performing the following non-limiting protocol. Without being bound by theory, the same protocol may be used for obtaining further *B. napus* plants:

a) embryos of, e.g., oilseed rape variety SR002201 whereof seeds have been deposited with the NCIMB, Aberdeen, UK, under Number NCIMB 41813, are incubated with an ALS inhibitor (e.g., $2\times10^{-7}$ M foramsulfuron);

b) optionally, surviving embryos (e.g. after 4, 5, 6, or 7 weeks) can be sub-cultured in, e.g., 2-4 intervals. Exemplary conditions are 25° C. and dim light at 12 h/12 h light/dark cycle;

c) following the selection on, e.g., $2\times10^{-7}$ M foramsulfuron, an embryo that was able to grow in presence of the ALS inhibitor (e.g., FM101 mutant) can be subjected to mutagenesis experiments such as incubating green tissue of the FM101 mutant in ethyl methanesulfonate (EMS);

d) surviving explants were subcultured on selective medium comprising, e.g., $10^{-4}$ M of a compound of formula I

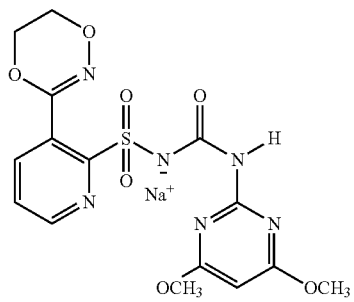

(I)

e) surviving explants can be regenerated to a plant.

In one embodiment, following the selection on a compound of formula (I), a highly resistant cell clone FM202 was isolated. The plants regenerated from the clone FM202 were able to grow in presence of the high concentration of ALS inhibitor. The ALS genes of the haploid plant FM202 were sequenced for the presence of a second mutation. The presence of a second single point mutation in the alanine 190 codon (corresponding to the alanine 205 codon in *A. thaliana* nomenclature) on the ALS I gene of rapeseed was confirmed by sequencing analysis. The double mutant plants FM202 can be propagated in vitro and treated with colchicine (e.g., 0.1%, 6 h) for chromosome doubling and later seed production.

Of course, all methods described herein are not limited to *B. napus* plants but are also suitable for the preparation of other *Brassica* plants.

Characterisation

Extraction and nucleic acid sequence analysis of the obtained mutant plants and mutated sequences 5, 6, 7, and 8 was performed by LGC Genomics GmbH, Berlin, Germany, according to standard protocols.

Agronomically Exploitable

The skilled person will understand that it is generally preferred that the *B. napus* plants of the present invention and parts thereof are agronomically exploitable.

"Agronomically exploitable" means that the *B. napus* plants and parts thereof are useful for agronomical purposes. For example, the *B. napus* plants should serve for the purpose of being useful for rapeseed oil production for, e.g., bio fuel or bar oil for chainsaws, animal feed or honey production. The term "agronomically exploitable" when used herein also includes that the *B. napus* plants of the present invention are preferably less sensitive against an ALS-inhibitor herbicide, more preferably it is at least 100 times less sensitive, more preferably, 500 times, even more preferably 1000 times and most preferably less than 2000 times. The ALS inhibitor herbicide is one or more described herein, preferably it is foramsulfuron either alone or in combination with one or more further ALS-inhibitor herbicide(s) either from the sub-class of the sulfonyurea herbicides or any other sub-class of the ALS-inhibitor herbicides, most preferably it is foramsulfuron in combination with a further sulfonylurea herbicide and/or an ALS-inhibitor of the sulfonylaminocarbonyltriazolinone herbicide sub-class.

Preferably, agronomically exploitable *B. napus* plants of the present invention are fully fertile, more preferably have wild-type fertility.

Another aspect of the present invention is the use of the *B. napus* plant described herein and/or the harvestable parts or propagation material described herein for the manufacture/breeding of *B. napus* plants. Methods for the manufacture/breeding of *B. napus* plants are described herein elsewhere. Such manufacture/breeding methods may be used to generate *B. napus* plants of the present invention further comprising novel plant traits such as stress-resistance, like but not limited to drought, heat, cold, or salt stress and the like.

In a still further aspect, the present invention envisages the use of the herbicide tolerant *B. napus* plant described herein and/or harvestable parts or propagation material derived thereof in a screening method for the selection of ALS inhibitor herbicides.

A better understanding of the present invention and of its many advantages will be had from the following examples, offered for illustrative purposes only, and are not intended to limit the scope of the present invention in any way.

Seed Deposits

A representative sample of seeds of oilseed rape line SR002201 were deposited by Bayer CropScienee AG on Feb. 21, 2011 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers: NCIMB 41813.

A representative sample of seeds of oilseed rape line FM202 were deposited by Bayer CropScience AG on Feb. 21, 2011 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers: NCIMB 41812.

The Applicant requests that samples of the biological material and any material derived therefrom be only released to a designated Expert in accordance with Rule 32(1) EPC or related legislation of countries or treaties having similar rules and regulation, until the mention of the grant of the patent, or for 20 years from the date of filing if the application is refused, withdrawn or deemed to be withdrawn.

Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

EXAMPLES

Mutant Isolation

Microspore Isolation and Embryo Induction

Unopened oilseed rape seed flower buds of sizes +/−3 mm have been isolated from donor plants of oilseed rape line SR002201 (NCIMB 41813).

The donor plants were grown till flowering in controlled environment in the greenhouse. The buds were surface sterilized 20 min in 5% NaOCl bleach and rinsed three times with sterile water.

Microspores were released from buds by mechanical squeezing in a mortar. The slurry was poured through a fine mesh with minimum pore size of 45 µm and washed through with liquid B5 medium (Gamborg et al. 1968). The filtrate was centrifuged for 3 min at 1,500 rpm two times, spores being re-suspended in fresh B5 medium each time.

The isolated microspores were finally suspended in liquid Lichter's medium (Lichter 1982) and plated at a concentration of 60,000-100,000 spores/mL. The microspores were cultured at 32° C. in dark for 3 days and then transferred to the culture room at 25° C. in low light intensity for embryo induction. The embryos were grown 2-3 weeks to reach morphological maturity (approximately 5 mm long).

Selection of Mutant FM101

The microspore derived embryos were transferred to agar (0.8%) solidified B5 medium comprising $2\times10^{-7}$ M of the ALS inhibitor herbicide foramsulfuron (CAS RN 173159-57-4). Six weeks later the surviving embryos were transferred onto fresh agar medium of the same composition and then sub-cultured in 2-4 intervals. The cultures were kept at 25° C. under dim light at 12 h/12 h light/dark cycle.

Preliminary, microspore derived embryos of the rapeseed line SR002201 (NCIMB 41813) were transferred to non-selective medium to check the viability of the embryos obtained from the isolated microspores. The in vitro cultured microspores divided and developed into embryos able to grow into normal haploid plantlets.

Following the selection on $2\times10^{-7}$ M foramsulfuron, one embryo was able to grow in presence of the ALS inhibitor and to regenerate to plant. The presence of a single point mutation in the tryptophan 556 codon (corresponding to the tryptophane 574 codon in *A. thaliana*) on the ALS III gene of rapeseed was confirmed by sequencing analysis. The same mutation was found in canola by Hattori et al. (1995). Prior transfer to the greenhouse, the haploid plants of the mutant FM101 were treated with colchicine (0.1%, 6 h) for chromosome doubling and later seed production. After colchicine treatment, the FM101 plants were transferred into sterile plant containers filled with wet, sterilized perlite, watered with half strength MS inorganic ingredients (Murashige, T. & Skoog, F. 1962) and cultured for one week till transplantation in soil.

Selection of Mutant FM202

The original FM101 mutant was maintained as tissue and shoot culture in vitro and used for EMS mutagenesis experiments. The green tissue was incubated in 0.2% ethyl methanesulfonate (EMS) solution for 16 h-20 h and cultured for 1 week on non-selective medium. Surviving explants were subcultured on selective medium comprising $10^{-4}$ M of a compound of formula I

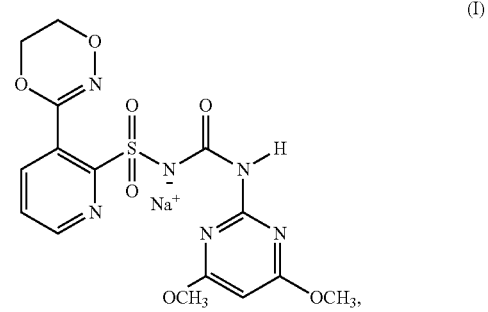 [SMILES: COc1cc(OC)nc(NC(=O)[N-]S(=O)(=O)c2ncccc2C2=NOCCO2)n1 ; [Na+]]

an inhibitory concentration of herbicide which prevented the growth of non-mutagenized FM101 tissue. Following the selection on a compound of formula (I), a highly resistant cell clone FM202 could be isolated. The plants regenerated from the clone FM202 were able to grow in presence of the high concentration of ALS inhibitor. The double mutant plants FM202 were propagated in vitro and treated with colchicine (0.1%, 6 h) for chromosome doubling and later seed production. After colchicine treatment, the FM202 plants were transferred into sterile plant containers filled with wet, sterilized perlite, watered with half strength MS inorganic ingredients and cultured for one week till transplantation in soil.

Seed Production of FM202

The FM202 plants transferred to the greenhouse were grown to maturity and self-pollinated for seeds production. The harvested seeds were used for herbicide trial.

Preparation of the Spray Mixtures

The individual components herbicide and surfactant with regard to type and application rate as stated in table I were added with stirring to a water application rate of 300 l/ha so that a homogeneous spray mixture was formed. The adjuvant Mero® (Bayer CropScience AG: active ingredient is 81% rapeseed oil methyl ester)) was always added to the spray liquids with a use rate of one l/ha.

Biological Examples

The abbreviations used herein below denote:
a.i.=active ingredient
g a.i./ha=grams of active substance/hectare
l/ha=liter/hectare
ALS-Inhibitors=Acetolactate Synthetase Inhibitors Seeds of *B. napus* were sown in a sandy loam soil and placed in a climate chamber in a greenhouse under good growth conditions (16 h light, temperature day 14° C., night: 8° C.). The plants were grown up to growth stage of BBCH 12 to BBCH 13. The plants were treated on a track sprayer with spray mixtures which had been prepared in accordance with the examples. After the treatment, the plants were returned to the climate chamber.

ALS-Inhibitor Injury on *B. napus*

Visual scoring 14 days after the application gave the results shown in Table 1. Visual scoring was carried out using a percentage scale of 0%=no damage to 100%=all plants dead.

The ALS-inhibitor tolerance of the mutant FM 202 compared to the wild type line SR002201 (NCIMB 41813) is clearly demonstrated in table 1.

TABLE 1

| herbicide | g a.i./ha | Herbicide injury on *B. napus* [%] SR002201 | FM 202 |
|---|---|---|---|
| Foramsulfuron | 35 | 75 | 0 |
| Iodosulfuron | 7 | 95 | 0 |
| Thiencarbazone | 20 | 90 | 0 |
| Compound of formula (I) | 15 | 95 | 0 |
| Metsulfuron | 8 | 93 | 0 |
| Amidosulfuron | 30 | 93 | 0 |
| Ethoxysulfuron | 60 | 98 | 0 |
| Mesosulfuron | 15 | 90 | 0 |
| Chlorsulfuron | 9 | 97 | 0 |
| Tribenuron | 30 | 95 | 3 |
| Triflusulfuron | 20 | 65 | 0 |
| Imazamox | 40 | 93 | 0 |

PI50-Values (=Negative Logarithm of the Molar Concentration Inhibiting the Enzyme Activity by 50%) for *A. thaliana* Wild-Type, A205V-, W575L- and S653N-Mutant ALS Genes The coding sequences of the *Arabidopsis thaliana* wild-type and A205V-, W574L- and S653N-mutant ALS genes were cloned into Novagen pET-32a(+) vectors and the vectors transformed into *Escherichia coli* AD494 according to the instructions of the manufacturer. Bacteria were grown at 37° C. in LB-medium containing 100 mg/l carbenicillin and 25 mg/l canamycin, induced with 1 mM isopropyl-β-D-thiogalactopyranoside at an $OD_{600}$ of 0.6, cultivated for 16 hours at 18° C. and harvested by centrifugation. Bacterial pellets were resuspended in 100 mM sodium phosphate buffer pH 7.0 containing 0.1 mM thiamine-pyrophosphate, 1 mM $MgCl_2$, and 1 µM FAD at a concentration of 1 gram wet weight per 25 ml of buffer and disrupted by sonification. The crude protein extract obtained after centrifugation was used for ALS activity measurements.

ALS assays were carried out in 96-well microliter plates using a modification of the procedure described by Ray (1984), Plant Physiol 75:827-831. The reaction mixture contained 20 mM potassium phosphate buffer pH 7.0, 20 mM sodium pyruvate, 0.45 mM thiamine-pyrophosphate, 0.45 mM 9 µM FAD, ALS enzyme and various concentrations of ALS inhibitors in a final volume of 90 µl. Assays were initiated by adding enzyme and terminated after 75 min incubation at 30° C. by the addition of 40 µl 0.5 M $H_2SO_4$. After 60 min at room temperature 80 µl of a solution of 1.4% α-naphtol and 0.14% creatine in 0.7 M NaOH was added and after an additional 45 min incubation at room temperature the absorbance was determined at 540 nm. pI50-values for inhibition of ALS were determined as described by Ray (1984), using the XLFit Excel add-in version 4.3.1 curve fitting program of ID Business Solutions Limited.

| Name | ALS PI50 WT | st. dev. | ALS PI50 W574L | st. dev. | ALS PI50 A205V | st. dev. | ALS PI50 S653N | st. dev. |
|---|---|---|---|---|---|---|---|---|
| Amidosulfuron | 6.7 | 0.2 | <4 | | 4.9 | 0.3 | 8.9 | |
| Bispyribac-sodium | 7.8 | 0.2 | 5.1 | | 7.0 | | 6.8 | |
| Ethoxysulfuron | 8.0 | 0.9 | <4 | | 6.0 | 0.8 | 7.8 | |
| Flazasulfuron | 8.6 | 0.5 | 5.5 | 0.2 | 7.8 | | n.m. | |
| Florasulam | 7.9 | 0.1 | 4.6 | 0.1 | 6.1 | | 7.6 | |
| Flupyrsulfuron-methyl | 8.4 | | 5.4 | 0.1 | 7.5 | 0.1 | n.m. | |
| Foramsulfuron | 8.2 | 0.2 | 4.3 | 0.0 | 6.3 | 0.1 | 7.3 | |
| Imazamox | 5.4 | 0.2 | <4 | | <4 | | <4 | |
| Iodosulfuron-methy-sodium | 8.7 | 0.4 | 5.8 | 0.2 | 6.4 | 0.3 | 7.6 | |
| Mesosulfuron-methyl | 9.1 | 0.5 | 4.4 | 0.1 | 6.6 | 0.1 | 7.7 | |
| Metosulam | 8.5 | 0.1 | 4.7 | 0.2 | 6.1 | | 7.4 | |
| Metsulfuron-methyl | 8.0 | 0.2 | 5.0 | 0.3 | 6.0 | 0.2 | 7.3 | |
| Nicosulfuron | 7.2 | 0.1 | <4 | | 6.0 | | 5.8 | |
| Propoxycarbazone | 7.9 | 0.2 | 5.2 | 0.1 | 6.7 | | 6.5 | |
| Rimsulfuron | 8.0 | | 5.0 | 0.1 | 6.8 | | 8.6 | |

-continued

| Name | ALS PI50 WT | st. dev. | ALS PI50 W574L | st. dev. | ALS PI50 A205V | st. dev. | ALS PI50 S653N | st. dev. |
|---|---|---|---|---|---|---|---|---|
| Sulfosulfuron | 7.8 | | <4 | | 5.9 | | 7.1 | |
| Thiencarbazone-methyl | 8.0 | 0.3 | 4.9 | 0.5 | 6.4 | 0.2 | 6.0 | |
| Thifensulfuron-Methyl | 7.5 | 0.2 | 4.2 | | 6.2 | | 6.8 | | n.m. = not measured
if no standard deviation is given, the IP50 value of a compound was measured only once.

The invention claimed is:

1. An ALS inhibitor herbicide tolerant *Brassica napus* plant or parts thereof comprising an ALS I polypeptide comprising an amino acid different from alanine at a position of said ALS I polypeptide corresponding to position 190 of SEQ ID NO: 2 and an ALS III polypeptide comprising an amino acid different from tryptophan at a position of said ALS III polypeptide corresponding to position 556 of SEQ ID NO: 4, wherein the *B. napus* plant or parts thereof are tolerant to foramsulfuronm, iodosulfuron, thiencarbazone, compound of formula (I), metsulfuron, amidosulfuron, ethoxysulfuron, mesosulfuron, chlorsulfuron, tribenuron, and imazamox, and wherein the compound of formula I is

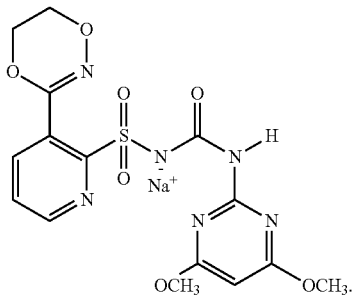

(I)

2. The *B. napus* plant or parts thereof according to claim 1, in which said ALS I polypeptide at a position corresponding to position 190 of SEQ ID NO: 2 instead of the naturally encoded amino acid alanine an amino acid selected from the group consisting of trypthophan (W), valine (V), methionine (M), isoleucine (I), leucine (L), proline (P), phenylalanine (F), arginine (R), lysine (K), histidine (H), aspartate (D), cysteine (C), glutamate (E), glycine (G), serine (S), threonine (T), tyrosine (Y) and glutamine (Q) and asparagine (N) and in which said ALS III polypeptide at a position corresponding to position 556 of SEQ ID NO: 4 instead of the naturally encoded amino acid tryptophan an amino acid selected from the group consisting of alanine (A), valine (V), methionine (M), isoleucine (I), leucine (L), proline (P), phenylalanine (F), arginine (R), lysine (K), histidine (H), aspartate (D), cysteine (C), glutamate (E), glycine (G), serine (S), threonine (T), tyrosine (Y) and glutamine (Q) and asparagine (N).

3. The *B. napus* plant or parts thereof according to claim 1, wherein the amino acid substitution in said ALS I polypeptide is Ala190Val.

4. The *B. napus* plant or parts thereof according to claim 1, wherein the amino acid substitution in said ALS III polypeptide is Trp556Leu.

5. The *B. napus* plant or parts thereof according to claim 1, wherein an ALS I polypeptide comprising an amino acid different from alanine at a position of said ALS I polypeptide corresponding to position 190 of SEQ ID NO: 2 is at least 95% identical to SEQ ID NO: 6 and has at least 20% ALS activity compared to ALS activity of a protein having SEQ ID NO:2 and wherein an ALS III polypeptide comprising an amino acid different from tryptophan at a position of said ALS III polypeptide corresponding to position 556 of SEQ ID NO: 4 is at least 95% identical to SEQ ID NO: 8 and has at least 20% ALS activity compared to ALS activity of a protein having SEQ ID NO:4.

6. The *B. napus* plant or parts thereof according to claim 5, wherein said ALS I polypeptide is identical to SEQ ID NO: 6 and wherein said ALS III polypeptide is identical to SEQ ID NO: 8.

7. The *B. napus* plant or parts thereof according to claim 1, which are tolerant to one or more ALS-inhibitor herbicides belonging to the group consisting of sulfonylurea herbicides, sulfonylaminocarbonyltriazolinone herbicides, imidazolinone herbicides, triazolopyrimidine herbicides, and pyrimidinyl(thio)benzoate herbicides.

8. The *B. napus* plant or parts thereof according to claim 1, which are homozygous for the non-transgenic mutation in the ALS I alleles encoding an ALS I polypeptide comprising an amino acid different from alanine at a position corresponding to position 190 of SEQ ID NO: 2, and for the non-transgenic mutation in the ALS III alleles encoding an ALS III polypeptide comprising an amino acid different from tryptophan at a position corresponding to position 556 of SEQ ID NO: 4.

9. The parts of the *B. napus* plant according to claim 1, wherein the parts are organs, tissues, cells or seeds.

10. An ALS inhibitor herbicide tolerant *Brassica napus* plant or parts thereof according to claim 1 produced by subjecting a *Brassica napus* plant to a mutagenic substance or radiation.

11. A *B. napus* plant designated FM202, representative seeds of which have been deposited under NCIMB accession number NCIMB 41812, or progeny thereof obtained by further breeding with said plant wherein said progeny contains an ALS I polypeptide comprising an amino acid different from alanine at a position of said ALS I polypeptide corresponding to position 190 of SEQ ID NO: 2 and an ALS III polypeptide comprising an amino acid different from tryptophan at a position of said ALS III polypeptide corresponding to position 556 of SEQ ID NO: 4.

12. Method of producing an ALS inhibitor herbicide tolerant *Brassica napus* plant or parts thereof according to claim 1 which method comprises a mutation of the genome of a *B. napus* plant by mutagenic substances or radiation.

13. A method of producing a hybrid seed, comprising crossing a parent *B. napus* plant according to claim 1 with a second parent *Brassica* plant and harvesting a resultant hybrid seed.

14. A hybrid plant produced from crossing a parent *B. napus* plant according to claim 1 with a second parent *Brassica* plant and harvesting a resultant hybrid seed and growing said seed to said hybrid plant, wherein said hybrid plant having at least an ALS I polypeptide comprising an amino acid different from alanine at a position of said ALS I polypeptide corresponding to position 205 of SEQ ID NO: 10 and an ALS III polypeptide comprising an amino acid different from tryptophan at a position of said ALS III polypeptide corresponding to position 574 of SEQ ID NO: 10.

15. Rapeseed oil produced by a plant according to claim 1.

16. The *B. napus* plant or parts thereof according to claim 2, wherein the amino acid substitution in said ALS I polypeptide is Ala190Val.

17. The *B. napus* plant or parts thereof according to claim 2, wherein the amino acid substitution in said ALS III polypeptide is Trp556Leu.

18. The *B. napus* plant or parts thereof according to claim 3, wherein the amino acid substitution in said ALS III polypeptide is Trp556Leu.

19. The *B. napus* plant or parts thereof according to claim 2, wherein an ALS I polypeptide comprising an amino acid different from alanine at a position of said ALS I polypeptide corresponding to position 190 of SEQ ID NO: 2 is at least 95% identical to SEQ ID NO: 6, and has at least 20% ALS activity compared to ALS activity of a protein having SEQ ID NO:2 and wherein an ALS III polypeptide comprising an amino acid different from tryptophan at a position of said ALS III polypeptide corresponding to position 556 of SEQ ID NO: 4 is at least 95% identical to SEQ ID NO: 8 and has at least 20% ALS activity compared to ALS activity of a protein having SEQ ID NO:4.

20. The *B. napus* plant or parts thereof according to claim 3, wherein an ALS I polypeptide comprising an amino acid different from alanine at a position of said ALS I polypeptide corresponding to position 190 of SEQ ID NO: 2 is at least 95% identical to SEQ ID NO: 6 and has at least 20% ALS activity compared to ALS activity of a protein having SEQ ID NO:2 and wherein an ALS III polypeptide comprising an amino acid different from tryptophan at a position of said ALS III polypeptide corresponding to position 556 of SEQ ID NO: 4 is at least 95% identical to SEQ ID NO: 8 and has at least 20% ALS activity compared to ALS activity of a protein having SEQ ID NO:4.

* * * * *

SEQUENCE LISTING

<160> NUMBER OF SEQ ID NOS: 10

<210> SEQ ID NO 1
<211> LENGTH: 1968
<212> TYPE: DNA
<213> ORGANISM: Brassica napus

<400> SEQUENCE: 1

```
atggcggcgg caacatcgtc ttctccgatc tccttaaccg ctaaaccttc ttccaaatcc      60
cctctaccca tttccagatt ctcccttccc ttctccttaa ccccacagaa agactcctcc     120
cgtctccacc gtcctctcgc catctccgcc gttctcaact cacccgtcaa tgtcgcacct     180
ccttcccctg aaaaaaccga caagaacaag actttcgtct cccgctacgc tcccgacgag     240
ccccgcaagg gtgctgatat cctcgtcgaa gccctcgagc gtcaaggcgt cgaaaccgtc     300
tttgcttatc ccggaggtgc ttccatggag atccaccaag ccttgactcg ctcctccacc     360
atccgtaacg tccttccccg tcacgaacaa ggaggagtct tcgccgccga gggttacgct     420
cgttcctccg gcaaaccggg aatctgcata gccacttcgg gtcccggagc taccaacctc     480
gtcagcgggt tagcagacgc gatgcttgac agtgttcctc ttgtcgccat tacaggacag     540
gtccctcgcc ggatgatcgg tactgacgcc ttccaagaga caccaatcgt tgaggtaacg     600
aggtctatta cgaaacataa ctatttggtg atggatgttg atgacatacc taggatcgtt     660
caagaagctt tctttctagc tacttccggt agacccggac cggttttggt tgatgttcct     720
aaggatattc agcagcagct tgcgattcct aactgggatc aacctatgcg cttacctggc     780
tacatgtcta ggttgcctca gcctccggaa gtttctcagt taggtcagat cgttaggttg     840
atctcggagt ctaagaggcc tgttttgtac gttggtggtg aagcttgaa ctcgagtgaa     900
gaactgggga gatttgtcga gcttactggg atccccgttg cgagtacttt gatgggggctt     960
ggctcttatc cttgtaacga tgagttgtcc ctgcagatgc ttggcatgca cgggactgtg    1020
tatgctaact acgctgtgga gcatagtgat ttgttgctgg cgtttggtgt taggtttgat    1080
gaccgtgtca cgggaaaagct cgaggctttc gctagcaggg ctaaaattgt gcacatagac    1140
attgattctg ctgagattgg gaagaataag acacctcacg tgtctgtgtg tggtgatgta    1200
aagctggctt tgcaagggat gaacaaggtt cttgagaacc gggcggagga gctcaagctt    1260
gatttcggtg tttggaggag tgagttgagc gagcagaaac agaagttccc tttgagcttc    1320
aaaacgtttg gagaagccat tcctccgcag tacgcgattc agatcctcga cgagctaacc    1380
gaagggaagg caattatcag tactggtgtt ggacagcatc agatgtgggc ggcgcagttt    1440
tacaagtaca ggaagccgag acagtggctg tcgtcatcag gcctcggagc tatgggtttt    1500
ggacttcctg ctgcgattgg agcgtctgtg gcgaaccctg atgcgattgt tgtggatatt    1560
gacggtgatg gaagcttcat aatgaacgtt caagagctgg ccacaatccg tgtagagaat    1620
```

```
cttcctgtga agatactctt gttaaacaac cagcatcttg ggatggtcat gcaatgggaa      1680
gatcggttct acaaagctaa cagagctcac acttatctcg gggacccggc aagggagaac      1740
gagatcttcc ctaacatgct gcagtttgca ggagcttgcg ggattccagc tgcgagagtg      1800
acgaagaaag aagaactccg agaagctatt cagacaatgc tggatacacc aggaccatac      1860
ctgttggatg tgatatgtcc gcaccaagaa catgtgttac cgatgatccc aagtggtggc      1920
actttcaaag atgtaataac agaaggggat ggtcgcacta agtactga                   1968
```

<210> SEQ ID NO 2
<211> LENGTH: 655
<212> TYPE: PRT
<213> ORGANISM: Brassica napus

<400> SEQUENCE: 2

```
Met Ala Ala Ala Thr Ser Ser Pro Ile Ser Leu Thr Ala Lys Pro
1               5                   10                  15

Ser Ser Lys Ser Pro Leu Pro Ile Ser Arg Phe Ser Leu Pro Phe Ser
            20                  25                  30

Leu Thr Pro Gln Lys Asp Ser Arg Leu His Arg Pro Leu Ala Ile
        35                  40                  45

Ser Ala Val Leu Asn Ser Pro Val Asn Val Ala Pro Pro Ser Pro Glu
    50                  55                  60

Lys Thr Asp Lys Asn Lys Thr Phe Val Ser Arg Tyr Ala Pro Asp Glu
65                  70                  75                  80

Pro Arg Lys Gly Ala Asp Ile Leu Val Glu Ala Leu Glu Arg Gln Gly
                85                  90                  95

Val Glu Thr Val Phe Ala Tyr Pro Gly Gly Ala Ser Met Glu Ile His
            100                 105                 110

Gln Ala Leu Thr Arg Ser Ser Thr Ile Arg Asn Val Leu Pro Arg His
        115                 120                 125

Glu Gln Gly Gly Val Phe Ala Ala Glu Gly Tyr Ala Arg Ser Ser Gly
    130                 135                 140

Lys Pro Gly Ile Cys Ile Ala Thr Ser Gly Pro Gly Ala Thr Asn Leu
145                 150                 155                 160

Val Ser Gly Leu Ala Asp Ala Met Leu Asp Ser Val Pro Leu Val Ala
                165                 170                 175

Ile Thr Gly Gln Val Pro Arg Arg Met Ile Gly Thr Asp Ala Phe Gln
            180                 185                 190

Glu Thr Pro Ile Val Glu Val Thr Arg Ser Ile Thr Lys His Asn Tyr
        195                 200                 205

Leu Val Met Asp Val Asp Asp Ile Pro Arg Ile Val Gln Glu Ala Phe
    210                 215                 220

Phe Leu Ala Thr Ser Gly Arg Pro Gly Pro Val Leu Val Asp Val Pro
225                 230                 235                 240

Lys Asp Ile Gln Gln Gln Leu Ala Ile Pro Asn Trp Asp Gln Pro Met
                245                 250                 255

Arg Leu Pro Gly Tyr Met Ser Arg Leu Pro Gln Pro Pro Glu Val Ser
            260                 265                 270

Gln Leu Gly Gln Ile Val Arg Leu Ile Ser Glu Ser Lys Arg Pro Val
        275                 280                 285

Leu Tyr Val Gly Gly Gly Ser Leu Asn Ser Ser Glu Glu Leu Gly Arg
    290                 295                 300

Phe Val Glu Leu Thr Gly Ile Pro Val Ala Ser Thr Leu Met Gly Leu
305                 310                 315                 320
```

Gly Ser Tyr Pro Cys Asn Asp Glu Leu Ser Leu Gln Met Leu Gly Met
                325                 330                 335

His Gly Thr Val Tyr Ala Asn Tyr Ala Val Glu His Ser Asp Leu Leu
            340                 345                 350

Leu Ala Phe Gly Val Arg Phe Asp Asp Arg Val Thr Gly Lys Leu Glu
        355                 360                 365

Ala Phe Ala Ser Arg Ala Lys Ile Val His Ile Asp Ile Asp Ser Ala
370                 375                 380

Glu Ile Gly Lys Asn Lys Thr Pro His Val Ser Val Cys Gly Asp Val
385                 390                 395                 400

Lys Leu Ala Leu Gln Gly Met Asn Lys Val Leu Glu Asn Arg Ala Glu
                405                 410                 415

Glu Leu Lys Leu Asp Phe Gly Val Trp Arg Ser Glu Leu Ser Glu Gln
                420                 425                 430

Lys Gln Lys Phe Pro Leu Ser Phe Lys Thr Phe Gly Glu Ala Ile Pro
                435                 440                 445

Pro Gln Tyr Ala Ile Gln Ile Leu Asp Glu Leu Thr Glu Gly Lys Ala
    450                 455                 460

Ile Ile Ser Thr Gly Val Gly Gln His Gln Met Trp Ala Ala Gln Phe
465                 470                 475                 480

Tyr Lys Tyr Arg Lys Pro Arg Gln Trp Leu Ser Ser Ser Gly Leu Gly
                485                 490                 495

Ala Met Gly Phe Gly Leu Pro Ala Ala Ile Gly Ala Ser Val Ala Asn
                500                 505                 510

Pro Asp Ala Ile Val Val Asp Ile Asp Gly Asp Gly Ser Phe Ile Met
                515                 520                 525

Asn Val Gln Glu Leu Ala Thr Ile Arg Val Glu Asn Leu Pro Val Lys
                530                 535                 540

Ile Leu Leu Leu Asn Asn Gln His Leu Gly Met Val Met Gln Trp Glu
545                 550                 555                 560

Asp Arg Phe Tyr Lys Ala Asn Arg Ala His Thr Tyr Leu Gly Asp Pro
                565                 570                 575

Ala Arg Glu Asn Glu Ile Phe Pro Asn Met Leu Gln Phe Ala Gly Ala
                580                 585                 590

Cys Gly Ile Pro Ala Ala Arg Val Thr Lys Lys Glu Glu Leu Arg Glu
                595                 600                 605

Ala Ile Gln Thr Met Leu Asp Thr Pro Gly Pro Tyr Leu Leu Asp Val
610                 615                 620

Ile Cys Pro His Gln Glu His Val Leu Pro Met Ile Pro Ser Gly Gly
625                 630                 635                 640

Thr Phe Lys Asp Val Ile Thr Glu Gly Asp Gly Arg Thr Lys Tyr
                645                 650                 655

<210> SEQ ID NO 3
<211> LENGTH: 1959
<212> TYPE: DNA
<213> ORGANISM: Brassica napus

<400> SEQUENCE: 3
atggcggcgg caacatcgtc ttctccgatc tccttaaccg ctaaaccttc ttccaaatcc      60
cctctaccca tttccagatt ctcccttccc ttctccttaa ccccacagaa accctcctcc     120
cgtctccacc gtccactcgc catctccgcc gttctcaact cacccgtcaa tgtcgcacct     180
gaaaaaaccg acaagatcaa gactttcatc tcccgctacg ctcccgacga gccccgcaag     240

-continued

```
ggtgctgata tcctcgtgga agccctcgag cgtcaaggcg tcgaaaccgt cttcgcttat    300
cccggaggtg cctccatgga gatccaccaa gccttgactc gctcctccac catccgtaac    360
gtcctccccc gtcacgaaca aggaggagtc ttcgccgccg agggttacgc tcgttcctcc    420
ggcaaaccgg gaatctgcat agccacttcg ggtcccggag ctaccaacct cgtcagcggg    480
ttagccgacg cgatgcttga cagtgttcct ctcgtcgcca tcacaggaca ggtccctcgc    540
cggatgatcg gtactgacgc gttccaagag acgccaatcg ttgaggtaac gaggtctatt    600
acgaaacata actatctggt gatggatgtt gatgacatac ctaggatcgt tcaagaagca    660
ttctttctag ctacttccgg tagacccgga ccggttttgg ttgatgttcc taaggatatt    720
cagcagcagc ttgcgattcc taactgggat caacctatgc gcttgcctgg ctacatgtct    780
aggctgcctc agccaccgga gtttctcag ttaggccaga tcgttaggtt gatctcggag    840
tctaagaggc ctgttttgta cgttggtggt ggaagcttga actcgagtga agaactgggg    900
agatttgtcg agcttactgg gatccctgtt gcgagtacgt tgatgggggct tggctcttat    960 ccttgtaacg atgagttgtc cctgcagatg cttggcatgc acgggactgt gtatgctaac   1020
tacgctgtgg agcatagtga tttgttgctg gcgtttggtg ttaggtttga tgaccgtgtc   1080
acgggaaagc tcgaggcgtt tgcgagcagg gctaagattg tgcacataga cattgattct   1140
gctgagattg ggaagaataa gacacctcac gtgtctgtgt gtggtgatgt aaagctggct   1200
ttgcaaggga tgaacaaggt tcttgagaac cgggcggagg agctcaagct tgatttcggt   1260
gtttggagga gtgagttgag cgagcagaaa cagaagttcc cgttgagctt caaaacgttt   1320
ggagaagcca ttcctccgca gtacgcgatt caggtcctag acgagctaac ccaagggaag   1380
gcaattatca gtactggtgt tggacagcat cagatgtggg cggcgcagtt ttacaagtac   1440
aggaagccga ggcagtggct gtcgtcctca ggactcggag ctatgggttt cggacttcct   1500
gctgcgattg gagcgtctgt ggcgaaccct gatgcgattg ttgtggacat tgacggtgat   1560
ggaagcttca taatgaacgt tcaagagctg gccacaatcc gtgtagagaa tcttcctgtg   1620
aagatactct tgttaaacaa ccagcatctt gggatggtca tgcaatggga agatcggttc   1680
tacaaagcta acagagctca cacttatctc ggggacccgg caaggagaa cgagatcttc   1740 cctaacatgc tgcagtttgc aggagcttgc gggattccag ctgcgagagt gacgaagaaa   1800
gaagaactcc gagaagctat tcagacaatg ctggatacac ctggaccgta cctgttggat   1860
gtcatctgtc cgcaccaaga acatgtgtta ccgatgatcc caagtggtgg cactttcaaa   1920
gatgtaataa ccgaagggga tggtcgcact aagtactga                          1959
```

<210> SEQ ID NO 4
<211> LENGTH: 652
<212> TYPE: PRT
<213> ORGANISM: Brassica napus

<400> SEQUENCE: 4

```
Met Ala Ala Ala Thr Ser Ser Pro Ile Ser Leu Thr Ala Lys Pro
1               5                  10                  15

Ser Ser Lys Ser Pro Leu Pro Ile Ser Arg Phe Ser Leu Pro Phe Ser
                20                  25                  30

Leu Thr Pro Gln Lys Pro Ser Ser Arg Leu His Arg Pro Leu Ala Ile
        35                  40                  45

Ser Ala Val Leu Asn Ser Pro Val Asn Val Ala Pro Glu Lys Thr Asp
    50                  55                  60
```

```
Lys Ile Lys Thr Phe Ile Ser Arg Tyr Ala Pro Asp Glu Pro Arg Lys
 65                  70                  75                  80

Gly Ala Asp Ile Leu Val Glu Ala Leu Glu Arg Gln Gly Val Glu Thr
                 85                  90                  95

Val Phe Ala Tyr Pro Gly Gly Ala Ser Met Glu Ile His Gln Ala Leu
            100                 105                 110

Thr Arg Ser Ser Thr Ile Arg Asn Val Leu Pro Arg His Glu Gln Gly
        115                 120                 125

Gly Val Phe Ala Ala Glu Gly Tyr Ala Arg Ser Ser Gly Lys Pro Gly
    130                 135                 140

Ile Cys Ile Ala Thr Ser Gly Pro Gly Ala Thr Asn Leu Val Ser Gly
145                 150                 155                 160

Leu Ala Asp Ala Met Leu Asp Ser Val Pro Leu Val Ala Ile Thr Gly
                165                 170                 175

Gln Val Pro Arg Arg Met Ile Gly Thr Asp Ala Phe Gln Glu Thr Pro
                180                 185                 190

Ile Val Glu Val Thr Arg Ser Ile Thr Lys His Asn Tyr Leu Val Met
            195                 200                 205

Asp Val Asp Asp Ile Pro Arg Ile Val Gln Glu Ala Phe Phe Leu Ala
210                 215                 220

Thr Ser Gly Arg Pro Gly Pro Val Leu Val Asp Val Pro Lys Asp Ile
225                 230                 235                 240

Gln Gln Gln Leu Ala Ile Pro Asn Trp Asp Gln Pro Met Arg Leu Pro
                245                 250                 255

Gly Tyr Met Ser Arg Leu Pro Gln Pro Pro Glu Val Ser Gln Leu Gly
            260                 265                 270

Gln Ile Val Arg Leu Ile Ser Glu Ser Lys Arg Pro Val Leu Tyr Val
        275                 280                 285

Gly Gly Gly Ser Leu Asn Ser Ser Glu Glu Leu Gly Arg Phe Val Glu
    290                 295                 300

Leu Thr Gly Ile Pro Val Ala Ser Thr Leu Met Gly Leu Gly Ser Tyr
305                 310                 315                 320

Pro Cys Asn Asp Glu Leu Ser Leu Gln Met Leu Gly Met His Gly Thr
                325                 330                 335

Val Tyr Ala Asn Tyr Ala Val Glu His Ser Asp Leu Leu Leu Ala Phe
            340                 345                 350

Gly Val Arg Phe Asp Asp Arg Val Thr Gly Lys Leu Glu Ala Phe Ala
        355                 360                 365

Ser Arg Ala Lys Ile Val His Ile Asp Ile Asp Ser Ala Glu Ile Gly
    370                 375                 380

Lys Asn Lys Thr Pro His Val Ser Val Cys Gly Asp Val Lys Leu Ala
385                 390                 395                 400

Leu Gln Gly Met Asn Lys Val Leu Glu Asn Arg Ala Glu Glu Leu Lys
                405                 410                 415

Leu Asp Phe Gly Val Trp Arg Ser Glu Leu Ser Glu Gln Lys Gln Lys
            420                 425                 430

Phe Pro Leu Ser Phe Lys Thr Phe Gly Glu Ala Ile Pro Pro Gln Tyr
        435                 440                 445

Ala Ile Gln Val Leu Asp Glu Leu Thr Gln Gly Lys Ala Ile Ile Ser
    450                 455                 460

Thr Gly Val Gly Gln His Gln Met Trp Ala Ala Gln Phe Tyr Lys Tyr
465                 470                 475                 480

Arg Lys Pro Arg Gln Trp Leu Ser Ser Ser Gly Leu Gly Ala Met Gly
```

|   |   |   | 485 |   |   |   | 490 |   |   |   | 495 |   |
|---|---|---|---|---|---|---|---|---|---|---|---|---|

Phe Gly Leu Pro Ala Ala Ile Gly Ala Ser Val Ala Asn Pro Asp Ala
                500                 505                 510

Ile Val Val Asp Ile Asp Gly Asp Gly Ser Phe Ile Met Asn Val Gln
            515                 520                 525

Glu Leu Ala Thr Ile Arg Val Glu Asn Leu Pro Val Lys Ile Leu Leu
        530                 535                 540

Leu Asn Asn Gln His Leu Gly Met Val Met Gln Trp Glu Asp Arg Phe
545                 550                 555                 560

Tyr Lys Ala Asn Arg Ala His Thr Tyr Leu Gly Asp Pro Ala Arg Glu
                565                 570                 575

Asn Glu Ile Phe Pro Asn Met Leu Gln Phe Ala Gly Ala Cys Gly Ile
            580                 585                 590

Pro Ala Ala Arg Val Thr Lys Lys Glu Glu Leu Arg Glu Ala Ile Gln
        595                 600                 605

Thr Met Leu Asp Thr Pro Gly Pro Tyr Leu Leu Asp Val Ile Cys Pro
    610                 615                 620

His Gln Glu His Val Leu Pro Met Ile Pro Ser Gly Gly Thr Phe Lys
625                 630                 635                 640

Asp Val Ile Thr Glu Gly Asp Gly Arg Thr Lys Tyr
                645                 650

<210> SEQ ID NO 5
<211> LENGTH: 1968
<212> TYPE: DNA
<213> ORGANISM: Brassica napu

<400> SEQUENCE: 5

```
atggcggcgg caacatcgtc ttctccgatc tccttaaccg ctaaaccttc ttccaaatcc    60
cctctaccca tttccagatt ctcccttccc ttctccttaa ccccacagaa agactcctcc   120
cgtctccacc gtcctctcgc catctccgcc gttctcaact cacccgtcaa tgtcgcacct   180
ccttcccctg aaaaaaccga caagaacaag actttcgtct cccgctacgc tcccgacgag   240
ccccgcaagg gtgctgatat cctcgtcgaa gccctcgagc gtcaaggcgt cgaaaccgtc   300
tttgcttatc ccggaggtgc ttccatggag atccaccaag ccttgactcg ctcctccacc   360
atccgtaacg tccttccccg tcacgaacaa ggaggagtct tcgccgccga gggttacgct   420
cgttcctccg gcaaaccggg aatctgcata gccacttcgg gtcccggagc taccaacctc   480
gtcagcgggt tagcagacgc gatgcttgac agtgttcctc ttgtcgccat acaggacag   540
gtccctcgcc ggatgatcgg tactgacgtc ttccaagaga caccaatcgt tgaggtaacg   600
aggtctatta cgaaacataa ctatttggtg atggatgttg atgacatacc taggatcgtt   660
caagaagctt tctttctagc tacttccggt agacccggac cggttttggt tgatgttcct   720
aaggatattc agcagcagct tgcgattcct aactgggatc aacctatgcg cttacctggc   780
tacatgtcta ggttgcctca gcctccggaa gtttctcagt taggtcagat cgttaggttg   840
atctcggagt ctaagaggcc tgttttgtac gttggtggtg aagcttgaa ctcgagtgaa   900
gaactgggga gatttgtcga gcttactggg atccccgttg cgagtacttt gatgggcttt   960
ggctcttatc cttgtaacga tgagttgtcc ctgcagatgc ttggcatgca cgggactgtg  1020
tatgctaact acgctgtgga gcatagtgat ttgttgctgg cgtttggtgt taggtttgat  1080
gaccgtgtca cggaaagct cgaggctttc gctagcaggg ctaaaattgt gcacatagac  1140
attgattctg ctgagattgg aagaataag acacctcacg tgtctgtgtg tggtgatgta  1200
```

```
aagctggctt tgcaagggat gaacaaggtt cttgagaacc gggcggagga gctcaagctt    1260
gatttcggtg tttggaggag tgagttgagc gagcagaaac agaagttccc tttgagcttc    1320
aaaacgtttg gagaagccat tcctccgcag tacgcgattc agatcctcga cgagctaacc    1380
gaagggaagg caattatcag tactggtgtt ggacagcatc agatgtgggc ggcgcagttt    1440
tacaagtaca ggaagccgag acagtggctg tcgtcatcag gcctcggagc tatgggtttt    1500
ggacttcctg ctgcgattgg agcgtctgtg gcgaaccctg atgcgattgt tgtggatatt    1560
gacggtgatg gaagcttcat aatgaacgtt caagagctgg ccacaatccg tgtagagaat    1620
cttcctgtga agatactctt gttaaacaac cagcatcttg gatggtcat gcaatgggaa    1680 gatcggttct acaaagctaa cagagctcac acttatctcg ggacccggc aagggagaac    1740 gagatcttcc ctaacatgct gcagtttgca ggagcttgcg ggattccagc tgcgagagtg    1800
acgaagaaag aagaactccg agaagctatt cagacaatgc tggatacacc aggaccatac    1860
ctgttggatg tgtatatgtcc gcaccaagaa catgtgttac cgatgatccc aagtggtggc    1920
actttcaaag atgtaataac agaaggggat ggtcgcacta agtactga                 1968
```

<210> SEQ ID NO 6
<211> LENGTH: 655
<212> TYPE: PRT
<213> ORGANISM: Brassica napus

<400> SEQUENCE: 6

```
Met Ala Ala Ala Thr Ser Ser Pro Ile Ser Leu Thr Ala Lys Pro
1               5                   10                  15

Ser Ser Lys Ser Pro Leu Pro Ile Ser Arg Phe Ser Leu Pro Phe Ser
                20                  25                  30

Leu Thr Pro Gln Lys Asp Ser Ser Arg Leu His Arg Pro Leu Ala Ile
            35                  40                  45

Ser Ala Val Leu Asn Ser Pro Val Asn Val Ala Pro Pro Ser Pro Glu
        50                  55                  60

Lys Thr Asp Lys Asn Lys Thr Phe Val Ser Arg Tyr Ala Pro Asp Glu
65                  70                  75                  80

Pro Arg Lys Gly Ala Asp Ile Leu Val Glu Ala Leu Glu Arg Gln Gly
                85                  90                  95

Val Glu Thr Val Phe Ala Tyr Pro Gly Gly Ala Ser Met Glu Ile His
                100                 105                 110

Gln Ala Leu Thr Arg Ser Ser Thr Ile Arg Asn Val Leu Pro Arg His
            115                 120                 125

Glu Gln Gly Gly Val Phe Ala Ala Glu Gly Tyr Ala Arg Ser Ser Gly
        130                 135                 140

Lys Pro Gly Ile Cys Ile Ala Thr Ser Gly Pro Gly Ala Thr Asn Leu
145                 150                 155                 160

Val Ser Gly Leu Ala Asp Ala Met Leu Asp Ser Val Pro Leu Val Ala
                165                 170                 175

Ile Thr Gly Gln Val Pro Arg Arg Met Ile Gly Thr Asp Val Phe Gln
                180                 185                 190

Glu Thr Pro Ile Val Glu Val Thr Arg Ser Ile Thr Lys His Asn Tyr
            195                 200                 205

Leu Val Met Asp Val Asp Asp Ile Pro Arg Ile Val Gln Glu Ala Phe
        210                 215                 220

Phe Leu Ala Thr Ser Gly Arg Pro Gly Pro Val Leu Val Asp Val Pro
225                 230                 235                 240
```

```
Lys Asp Ile Gln Gln Leu Ala Ile Pro Asn Trp Asp Gln Pro Met
            245                 250                 255

Arg Leu Pro Gly Tyr Met Ser Arg Leu Pro Gln Pro Glu Val Ser
            260                 265                 270

Gln Leu Gly Gln Ile Val Arg Leu Ile Ser Glu Ser Lys Arg Pro Val
            275                 280                 285

Leu Tyr Val Gly Gly Ser Leu Asn Ser Ser Glu Glu Leu Gly Arg
            290                 295                 300

Phe Val Glu Leu Thr Gly Ile Pro Val Ala Ser Thr Leu Met Gly Leu
305                 310                 315                 320

Gly Ser Tyr Pro Cys Asn Asp Glu Leu Ser Leu Gln Met Leu Gly Met
                    325                 330                 335

His Gly Thr Val Tyr Ala Asn Tyr Ala Val Glu His Ser Asp Leu Leu
                340                 345                 350

Leu Ala Phe Gly Val Arg Phe Asp Asp Arg Val Thr Gly Lys Leu Glu
            355                 360                 365

Ala Phe Ala Ser Arg Ala Lys Ile Val His Ile Asp Ile Asp Ser Ala
            370                 375                 380

Glu Ile Gly Lys Asn Lys Thr Pro His Val Ser Val Cys Gly Asp Val
385                 390                 395                 400

Lys Leu Ala Leu Gln Gly Met Asn Lys Val Leu Glu Asn Arg Ala Glu
                405                 410                 415

Glu Leu Lys Leu Asp Phe Gly Val Trp Arg Ser Glu Leu Ser Glu Gln
                420                 425                 430

Lys Gln Lys Phe Pro Leu Ser Phe Lys Thr Phe Gly Glu Ala Ile Pro
            435                 440                 445

Pro Gln Tyr Ala Ile Gln Ile Leu Asp Glu Leu Thr Glu Gly Lys Ala
            450                 455                 460

Ile Ile Ser Thr Gly Val Gly Gln His Gln Met Trp Ala Ala Gln Phe
465                 470                 475                 480

Tyr Lys Tyr Arg Lys Pro Arg Gln Trp Leu Ser Ser Ser Gly Leu Gly
                485                 490                 495

Ala Met Gly Phe Gly Leu Pro Ala Ala Ile Gly Ala Ser Val Ala Asn
                500                 505                 510

Pro Asp Ala Ile Val Val Asp Ile Asp Gly Asp Gly Ser Phe Ile Met
            515                 520                 525

Asn Val Gln Glu Leu Ala Thr Ile Arg Val Glu Asn Leu Pro Val Lys
            530                 535                 540

Ile Leu Leu Leu Asn Asn Gln His Leu Gly Met Val Met Gln Trp Glu
545                 550                 555                 560

Asp Arg Phe Tyr Lys Ala Asn Arg Ala His Thr Tyr Leu Gly Asp Pro
                565                 570                 575

Ala Arg Glu Asn Glu Ile Phe Pro Asn Met Leu Gln Phe Ala Gly Ala
            580                 585                 590

Cys Gly Ile Pro Ala Ala Arg Val Thr Lys Lys Glu Glu Leu Arg Glu
            595                 600                 605

Ala Ile Gln Thr Met Leu Asp Thr Pro Gly Pro Tyr Leu Leu Asp Val
            610                 615                 620

Ile Cys Pro His Gln Glu His Val Leu Pro Met Ile Pro Ser Gly Gly
625                 630                 635                 640

Thr Phe Lys Asp Val Ile Thr Glu Gly Asp Gly Arg Thr Lys Tyr
                645                 650                 655
```

<210> SEQ ID NO 7
<211> LENGTH: 1959
<212> TYPE: DNA
<213> ORGANISM: Brassica napus

<400> SEQUENCE: 7

| | | | | | |
|---|---|---|---|---|---|
| atggcggcgg | caacatcgtc | ttctccgatc | tccttaaccg | ctaaaccttc | ttccaaatcc | 60 |
| cctctaccca | tttccagatt | ctcccttccc | ttctccttaa | ccccacagaa | accctcctcc | 120 |
| cgtctccacc | gtcctctcgc | catctccgcc | gttctcaact | cacccgtcaa | tgtcgcacct | 180 |
| gaaaaaccg | acaagatcaa | gactttcatc | tcccgctacg | ctcccgacga | gccccgcaag | 240 |
| ggtgctgata | tcctcgtgga | agccctcgag | cgtcaaggcg | tcgaaaccgt | cttcgcttat | 300 |
| cccggaggtg | cctccatgga | gatccaccaa | gccttgactc | gctcctccac | catccgtaac | 360 |
| gtcctccccc | gtcacgaaca | aggaggagtc | ttcgccgccg | agggttacgc | tcgttcctcc | 420 |
| ggcaaaccgg | gaatctgcat | agccacttcg | ggtcccggag | ctaccaacct | cgtcagcggg | 480 |
| ttagccgacg | cgatgcttga | cagtgttcct | ctcgtcgcca | tcacaggaca | ggtccctcgc | 540 |
| cggatgatcg | gtactgacgc | cttccaagag | acgccaatcg | ttgaggtaac | gaggtctatt | 600 |
| acgaaacata | actatctggt | gatggatgtt | gatgacatac | ctaggatcgt | tcaagaagca | 660 |
| ttctttctag | ctacttccgg | tagacccgga | ccggttttgg | ttgatgttcc | taaggatatt | 720 |
| cagcagcagc | ttgcgattcc | taactgggat | caacctatgc | gcttgcctgg | ctacatgtct | 780 |
| aggctgcctc | agccaccgga | agtttctcag | ttaggccaga | tcgttaggtt | gatctcggag | 840 |
| tctaagaggc | ctgttttgta | cgttggtggt | ggaagcttga | actcgagtga | agaactgggg | 900 |
| agatttgtcg | agcttactgg | gatccctgtt | gcgagtacgt | tgatggggct | tggctcttat | 960 |
| ccttgtaacg | atgagttgtc | cctgcagatg | cttggcatgc | acgggactgt | gtatgctaac | 1020 |
| tacgctgtgg | agcatagtga | tttgttgctg | gcgtttggtg | ttaggtttga | tgaccgtgtc | 1080 |
| acgggaaagc | tcgaggcgtt | tgcgagcagg | gctaagattg | tgcacataga | cattgattct | 1140 |
| gctgagattg | gaagaataa | gacacctcac | gtgtctgtgt | gtggtgatgt | aaagctggct | 1200 |
| ttgcaaggga | tgaacaaggt | tcttgagaac | cgggcggagg | agctcaagct | tgatttcggt | 1260 |
| gtttggagga | gtgagttgag | cgagcagaaa | cagaagttcc | cgttgagctt | caaaacgttt | 1320 |
| ggagaagcca | ttcctccgca | gtacgcgatt | caggtcctag | acgagctaac | ccaagggaag | 1380 |
| gcaattatca | gtactggtgt | tggacagcat | cagatgtggg | cggcgcagtt | ttacaagtac | 1440 |
| aggaagccga | ggcagtggct | gtcgtcctca | ggactcggag | ctatgggttt | cggacttcct | 1500 |
| gctgcgattg | gagcgtctgt | ggcgaaccct | gatgcgattg | ttgtggacat | tgacggtgat | 1560 |
| ggaagcttca | taatgaacgt | tcaagagctg | gccacaatcc | gtgtagagaa | tcttcctgtg | 1620 |
| aagatactct | tgttaaacaa | ccagcatctt | gggatggtca | tgcaattgga | agatcggttc | 1680 |
| tacaaagcta | acagagctca | cacttatctc | ggggacccgg | caaggagaa | cgagatcttc | 1740 |
| cctaacatgc | tgcagtttgc | aggagcttgc | gggattccag | ctgcgagagt | gacgaagaaa | 1800 |
| gaagaactcc | gagaagctat | tcagacaatg | ctggatacac | ctggaccgta | cctgttggat | 1860 |
| gtcatctgtc | cgcaccaaga | acatgtgtta | ccgatgatcc | caagtggtgg | cactttcaaa | 1920 |
| gatgtaataa | ccgaaggga | tggtcgcact | aagtactga | | | 1959 |

<210> SEQ ID NO 8
<211> LENGTH: 652
<212> TYPE: PRT
<213> ORGANISM: Brassica napus

<400> SEQUENCE: 8

```
Met Ala Ala Ala Thr Ser Ser Pro Ile Ser Leu Thr Ala Lys Pro
1               5                   10                  15

Ser Ser Lys Ser Pro Leu Pro Ile Ser Arg Phe Ser Leu Pro Phe Ser
            20                  25                  30

Leu Thr Pro Gln Lys Pro Ser Ser Arg Leu His Arg Pro Leu Ala Ile
            35                  40                  45

Ser Ala Val Leu Asn Ser Pro Val Asn Val Ala Pro Glu Lys Thr Asp
        50                  55                  60

Lys Ile Lys Thr Phe Ile Ser Arg Tyr Ala Pro Asp Glu Pro Arg Lys
65                  70                  75                  80

Gly Ala Asp Ile Leu Val Glu Ala Leu Glu Arg Gln Gly Val Glu Thr
                85                  90                  95

Val Phe Ala Tyr Pro Gly Gly Ala Ser Met Glu Ile His Gln Ala Leu
            100                 105                 110

Thr Arg Ser Ser Thr Ile Arg Asn Val Leu Pro Arg His Glu Gln Gly
            115                 120                 125

Gly Val Phe Ala Ala Glu Gly Tyr Ala Arg Ser Ser Gly Lys Pro Gly
        130                 135                 140

Ile Cys Ile Ala Thr Ser Gly Pro Gly Ala Thr Asn Leu Val Ser Gly
145                 150                 155                 160

Leu Ala Asp Ala Met Leu Asp Ser Val Pro Leu Val Ala Ile Thr Gly
                165                 170                 175

Gln Val Pro Arg Arg Met Ile Gly Thr Asp Ala Phe Gln Glu Thr Pro
            180                 185                 190

Ile Val Glu Val Thr Arg Ser Ile Thr Lys His Asn Tyr Leu Val Met
            195                 200                 205

Asp Val Asp Asp Ile Pro Arg Ile Val Gln Glu Ala Phe Phe Leu Ala
        210                 215                 220

Thr Ser Gly Arg Pro Gly Pro Val Leu Val Asp Val Pro Lys Asp Ile
225                 230                 235                 240

Gln Gln Gln Leu Ala Ile Pro Asn Trp Asp Gln Pro Met Arg Leu Pro
                245                 250                 255

Gly Tyr Met Ser Arg Leu Pro Gln Pro Pro Glu Val Ser Gln Leu Gly
            260                 265                 270

Gln Ile Val Arg Leu Ile Ser Glu Ser Lys Arg Pro Val Leu Tyr Val
            275                 280                 285

Gly Gly Gly Ser Leu Asn Ser Ser Glu Glu Leu Gly Arg Phe Val Glu
        290                 295                 300

Leu Thr Gly Ile Pro Val Ala Ser Thr Leu Met Gly Leu Gly Ser Tyr
305                 310                 315                 320

Pro Cys Asn Asp Glu Leu Ser Leu Gln Met Leu Gly Met His Gly Thr
                325                 330                 335

Val Tyr Ala Asn Tyr Ala Val Glu His Ser Asp Leu Leu Leu Ala Phe
            340                 345                 350

Gly Val Arg Phe Asp Asp Arg Val Thr Gly Lys Leu Glu Ala Phe Ala
        355                 360                 365

Ser Arg Ala Lys Ile Val His Ile Asp Ile Asp Ser Ala Glu Ile Gly
            370                 375                 380

Lys Asn Lys Thr Pro His Val Ser Val Cys Gly Asp Val Lys Leu Ala
385                 390                 395                 400

Leu Gln Gly Met Asn Lys Val Leu Glu Asn Arg Ala Glu Glu Leu Lys
```

|  | 405 |  |  |  | 410 |  |  |  | 415 |  |  |
|---|---|---|---|---|---|---|---|---|---|---|---|

Leu Asp Phe Gly Val Trp Arg Ser Glu Leu Ser Glu Gln Lys Gln Lys
                420                 425                 430

Phe Pro Leu Ser Phe Lys Thr Phe Gly Glu Ala Ile Pro Pro Gln Tyr
                435                 440                 445

Ala Ile Gln Val Leu Asp Glu Leu Thr Gln Gly Lys Ala Ile Ile Ser
        450                 455                 460

Thr Gly Val Gly Gln His Gln Met Trp Ala Ala Gln Phe Tyr Lys Tyr
465                 470                 475                 480

Arg Lys Pro Arg Gln Trp Leu Ser Ser Gly Leu Gly Ala Met Gly
                485                 490                 495

Phe Gly Leu Pro Ala Ala Ile Gly Ala Ser Val Ala Asn Pro Asp Ala
                500                 505                 510

Ile Val Val Asp Ile Asp Gly Asp Gly Ser Phe Ile Met Asn Val Gln
                515                 520                 525

Glu Leu Ala Thr Ile Arg Val Glu Asn Leu Pro Val Lys Ile Leu Leu
        530                 535                 540

Leu Asn Asn Gln His Leu Gly Met Val Met Gln Leu Glu Asp Arg Phe
545                 550                 555                 560

Tyr Lys Ala Asn Arg Ala His Thr Tyr Leu Gly Asp Pro Ala Arg Glu
                565                 570                 575

Asn Glu Ile Phe Pro Asn Met Leu Gln Phe Ala Gly Ala Cys Gly Ile
                580                 585                 590

Pro Ala Ala Arg Val Thr Lys Lys Glu Glu Leu Arg Glu Ala Ile Gln
                595                 600                 605

Thr Met Leu Asp Thr Pro Gly Pro Tyr Leu Leu Asp Val Ile Cys Pro
610                 615                 620

His Gln Glu His Val Leu Pro Met Ile Pro Ser Gly Gly Thr Phe Lys
625                 630                 635                 640

Asp Val Ile Thr Glu Gly Asp Gly Arg Thr Lys Tyr
                645                 650

<210> SEQ ID NO 9
<211> LENGTH: 2013
<212> TYPE: DNA
<213> ORGANISM: Arabidopsis thaliana

<400> SEQUENCE: 9

| atggcggcgg | caacaacaac | aacaacaaca | tcttcttcga | tctccttctc | caccaaacca | 60 |
| tctccttcct | cctccaaatc | accattacca | atctccagat | tctccctccc | attctcccta | 120 |
| aaccccaaca | aatcatcctc | ctcctcccgc | cgccgcggta | tcaaatccag | ctctccctcc | 180 |
| tccatctccg | ccgtgctcaa | cacaaccacc | aatgtgacaa | ccactccctc | tccaaccaaa | 240 |
| cctaccaaac | ccgaaacatt | catctcccga | ttcgctccag | atcaaccccg | caaaggcgct | 300 |
| gatatcctcg | tcgaagcttt | agaacgtcaa | ggcgtagaaa | ccgtattcgc | ttaccctgga | 360 |
| ggtgcatcaa | tggagattca | ccaagcctta | acccgctctt | cctcaatccg | taacgtcctt | 420 |
| cctcgtcacg | aacaaggagg | tgtattcgca | gcagaaggat | acgctcgatc | ctcaggtaaa | 480 |
| ccaggtatct | gtatagccac | ttcaggtccc | ggagctacaa | atctcgttag | cggattagcc | 540 |
| gatgcgttgt | tagatagtgt | tcctcttgta | gcaatcacag | gacaagtccc | tcgtcgtatg | 600 |
| attggtacag | atgcgtttca | agagactccg | attgttgagg | taacgcgttc | gattacgaag | 660 |
| cataactatc | ttgtgatgga | tgttgaagat | atccctagga | ttattgagga | agctttcttt | 720 |

```
ttagctactt ctggtagacc tggacctgtt ttggttgatg ttcctaaaga tattcaacaa    780
cagcttgcga ttcctaattg ggaacaggct atgagattac ctggttatat gtctaggatg    840
cctaaacctc cggaagattc tcatttggag cagattgtta ggttgatttc tgagtctaag    900
aagcctgtgt tgtatgttgg tggtggttgt ttgaattcta gcgatgaatt gggtaggttt    960
gttgagctta cggggatccc tgttgcgagt acgttgatgg ggctgggatc ttatccttgt   1020
gatgatgagt tgtcgttaca tatgcttgga atgcatggga ctgtgtatgc aaattacgct   1080
gtggagcata gtgatttgtt gttggcgttt ggggtaaggt ttgatgatcg tgtcacgggt   1140
aagcttgagg cttttgctag tagggctaag attgttcata ttgatattga ctcggctgag   1200
attgggaaga ataagactcc tcatgtgtct gtgtgtggtg atgttaagct ggctttgcaa   1260
gggatgaata aggttcttga gaaccgagcg gaggagctta agcttgattt tggagtttgg   1320
aggaatgagt tgaacgtaca gaaacagaag tttccgttga gctttaagac gtttggggaa   1380
gctattcctc cacagtatgc gattaaggtc cttgatgagt tgactgatgg aaaagccata   1440
ataagtactg gtgtcgggca acatcaaatg tgggcggcgc agttctacaa ttacaagaaa   1500
ccaaggcagt ggctatcatc aggaggcctt ggagctatgg gatttggact tcctgctgcg   1560
attggagcgt ctgttgctaa ccctgatgcg atagttgtgg atattgacgg agatggaagc   1620
tttataatga atgtgcaaga gctagccact attcgtgtag agaatcttcc agtgaaggta   1680
ctttttattaa acaaccagca tcttggcatg ttatgcaat ggcaagatcg gttctacaaa   1740
gctaaccgag ctcacacatt tctcggggat ccggctcagg aggacgagat attcccgaac   1800
atgttgctgt ttgcagcagc ttgcgggatt ccagcggcga gggtgacaaa gaaagcagat   1860
ctccgagaag ctattcagac aatgctggat acaccaggac cttacctgtt ggatgtgatt   1920
tgtccgcacc aagaacatgt gttgccgatg atcccgagtg gtggcacttt caacgatgtc   1980
ataacggaag gagatggccg gattaaatac tga                                2013
```

<210> SEQ ID NO 10
<211> LENGTH: 670
<212> TYPE: PRT
<213> ORGANISM: Arabidopsis thaliana

<400> SEQUENCE: 10

```
Met Ala Ala Thr Thr Thr Thr Thr Ser Ser Ile Ser Phe
1               5                   10                  15

Ser Thr Lys Pro Ser Pro Ser Ser Lys Ser Pro Leu Pro Ile Ser
            20                  25                  30

Arg Phe Ser Leu Pro Phe Ser Leu Asn Pro Asn Lys Ser Ser Ser
        35                  40                  45

Ser Arg Arg Arg Gly Ile Lys Ser Ser Pro Ser Ser Ile Ser Ala
    50                  55                  60

Val Leu Asn Thr Thr Thr Asn Val Thr Thr Thr Pro Ser Pro Thr Lys
65                  70                  75                  80

Pro Thr Lys Pro Glu Thr Phe Ile Ser Arg Phe Ala Pro Asp Gln Pro
                85                  90                  95

Arg Lys Gly Ala Asp Ile Leu Val Glu Ala Leu Glu Arg Gln Gly Val
            100                 105                 110

Glu Thr Val Phe Ala Tyr Pro Gly Gly Ala Ser Met Glu Ile His Gln
        115                 120                 125

Ala Leu Thr Arg Ser Ser Ser Ile Arg Asn Val Leu Pro Arg His Glu
    130                 135                 140
```

-continued

```
Gln Gly Gly Val Phe Ala Ala Glu Gly Tyr Ala Arg Ser Ser Gly Lys
145                 150                 155                 160

Pro Gly Ile Cys Ile Ala Thr Ser Gly Pro Gly Ala Thr Asn Leu Val
            165                 170                 175

Ser Gly Leu Ala Asp Ala Leu Leu Asp Ser Val Pro Leu Val Ala Ile
                180                 185                 190

Thr Gly Gln Val Pro Arg Arg Met Ile Gly Thr Asp Ala Phe Gln Glu
        195                 200                 205

Thr Pro Ile Val Glu Val Thr Arg Ser Ile Thr Lys His Asn Tyr Leu
    210                 215                 220

Val Met Asp Val Glu Asp Ile Pro Arg Ile Ile Glu Glu Ala Phe Phe
225                 230                 235                 240

Leu Ala Thr Ser Gly Arg Pro Gly Pro Val Leu Val Asp Val Pro Lys
                245                 250                 255

Asp Ile Gln Gln Gln Leu Ala Ile Pro Asn Trp Glu Gln Ala Met Arg
            260                 265                 270

Leu Pro Gly Tyr Met Ser Arg Met Pro Lys Pro Pro Glu Asp Ser His
        275                 280                 285

Leu Glu Gln Ile Val Arg Leu Ile Ser Glu Ser Lys Lys Pro Val Leu
    290                 295                 300

Tyr Val Gly Gly Gly Cys Leu Asn Ser Ser Asp Glu Leu Gly Arg Phe
305                 310                 315                 320

Val Glu Leu Thr Gly Ile Pro Val Ala Ser Thr Leu Met Gly Leu Gly
                325                 330                 335

Ser Tyr Pro Cys Asp Asp Glu Leu Ser Leu His Met Leu Gly Met His
        340                 345                 350

Gly Thr Val Tyr Ala Asn Tyr Ala Val Glu His Ser Asp Leu Leu Leu
    355                 360                 365

Ala Phe Gly Val Arg Phe Asp Asp Arg Val Thr Gly Lys Leu Glu Ala
370                 375                 380

Phe Ala Ser Arg Ala Lys Ile Val His Ile Asp Ile Asp Ser Ala Glu
385                 390                 395                 400

Ile Gly Lys Asn Lys Thr Pro His Val Ser Val Cys Gly Asp Val Lys
            405                 410                 415

Leu Ala Leu Gln Gly Met Asn Lys Val Leu Glu Asn Arg Ala Glu Glu
        420                 425                 430

Leu Lys Leu Asp Phe Gly Val Trp Arg Asn Glu Leu Asn Val Gln Lys
    435                 440                 445

Gln Lys Phe Pro Leu Ser Phe Lys Thr Phe Gly Glu Ala Ile Pro Pro
450                 455                 460

Gln Tyr Ala Ile Lys Val Leu Asp Glu Leu Thr Asp Gly Lys Ala Ile
465                 470                 475                 480

Ile Ser Thr Gly Val Gly Gln His Gln Met Trp Ala Ala Gln Phe Tyr
            485                 490                 495

Asn Tyr Lys Lys Pro Arg Gln Trp Leu Ser Ser Gly Gly Leu Gly Ala
        500                 505                 510

Met Gly Phe Gly Leu Pro Ala Ala Ile Gly Ala Ser Val Ala Asn Pro
    515                 520                 525

Asp Ala Ile Val Val Asp Ile Asp Gly Asp Gly Ser Phe Ile Met Asn
530                 535                 540

Val Gln Glu Leu Ala Thr Ile Arg Val Glu Asn Leu Pro Val Lys Val
545                 550                 555                 560

Leu Leu Leu Asn Asn Gln His Leu Gly Met Val Met Gln Trp Gln Asp
```

```
              565                 570                 575
Arg Phe Tyr Lys Ala Asn Arg Ala His Thr Phe Leu Gly Asp Pro Ala
            580                 585                 590

Gln Glu Asp Glu Ile Phe Pro Asn Met Leu Leu Phe Ala Ala Ala Cys
        595                 600                 605

Gly Ile Pro Ala Ala Arg Val Thr Lys Lys Ala Asp Leu Arg Glu Ala
        610                 615                 620

Ile Gln Thr Met Leu Asp Thr Pro Gly Pro Tyr Leu Leu Asp Val Ile
625                 630                 635                 640

Cys Pro His Gln Glu His Val Leu Pro Met Ile Pro Ser Gly Gly Thr
                645                 650                 655

Phe Asn Asp Val Ile Thr Glu Gly Asp Gly Arg Ile Lys Tyr
                660                 665                 670
```